(12) United States Patent
Iqbal et al.

(10) Patent No.: US 10,080,778 B2
(45) Date of Patent: Sep. 25, 2018

(54) NEUROGENIC BRAIN-DERIVED NEUROTROPHIC FACTOR PEPTIDES

(71) Applicant: Research Foundation for Mental Hygiene, Inc., Menands, NY (US)

(72) Inventors: Khalid Iqbal, Staten Island, NY (US); Inge Grundke-Iqbal, Staten Island, NY (US)

(73) Assignee: Research Foundation For Mental Hygiene, Inc., Menands, NY (US)

( * ) Notice: Subject to any disclaimer, the term of this patent is extended or adjusted under 35 U.S.C. 154(b) by 24 days.

(21) Appl. No.: 15/297,386

(22) Filed: Oct. 19, 2016

(65) Prior Publication Data

US 2017/0028022 A1 Feb. 2, 2017

Related U.S. Application Data

(62) Division of application No. 13/939,352, filed on Jul. 11, 2013, now Pat. No. 9,512,178.

(60) Provisional application No. 61/670,325, filed on Jul. 11, 2012.

(51) Int. Cl.
| | |
|---|---|
| *A61K 38/18* | (2006.01) |
| *C07K 5/10* | (2006.01) |
| *C07K 5/103* | (2006.01) |
| *C07K 5/11* | (2006.01) |
| *C07K 5/113* | (2006.01) |
| *A61K 38/07* | (2006.01) |
| *A61K 38/00* | (2006.01) |

(52) U.S. Cl.
CPC ............ *A61K 38/185* (2013.01); *A61K 38/07* (2013.01); *C07K 5/10* (2013.01); *C07K 5/101* (2013.01); *C07K 5/1013* (2013.01); *C07K 5/1019* (2013.01); *C07K 5/1021* (2013.01); *A61K 38/00* (2013.01)

(58) Field of Classification Search
None
See application file for complete search history.

(56) References Cited

U.S. PATENT DOCUMENTS

2006/0002958 A1* 1/2006 Naylor ................ A61K 39/155
424/209.1

OTHER PUBLICATIONS

Cardenas-Aguayo et al. ("Neurogenic and neuroprotective effects of BDNF peptides in mouse hippocampal primary neuronal cell cultures," Jul. 2011, vol. 7, Issue 4, Supplement, Abstract #P3-423, p. S651 (Year: 2011).*
The website: web.archive.org/web/20080204224458/http://www.genscript.com/peptide_modification.html; 2 pages total (Year: 2008).*
Chanprapaph et al., Biochemical and Biophysical Research Communications 2005; 330: 1237-1246 (Year: 2005).*

* cited by examiner

*Primary Examiner* — Christina M Borgeest
(74) *Attorney, Agent, or Firm* — Bond Schoeneck & King, PLLC; David Nocilly

(57) ABSTRACT

Five tetra peptides corresponding to different active regions of brain derived neurotrophic factor (BDNF) that are neurotrophic and can modulate BDNF signaling in a partial agonist/antagonist way. The peptides offer a therapeutic approach to neural pathologies where BDNF levels are dysregulated.

7 Claims, 26 Drawing Sheets

Specification includes a Sequence Listing.

Pro BDNF sequence (SEQ ID NO: 6)

```
        10          20          30          40          50          60
MTILFLTMVI  SYFGCMKAAP  MKEANIRGQG  GLAYPGVRTH  GTLESVNGPK  AGSRGLTSLA 70          80          90         100         110         120
DTFEHVIEEL  LDEDQKVRPN  EENNKDADLY  TSRVMLSSQV  PLEPPLLFLL  EEYKNYLDAA 130         140         150         160         170         180
NMSMRVRRHS  DPA[RRGELSV  CDSISEWVTA  ADKKTAVDMS  GGTVTVLEKV  PVSKGQLKQY
             B-1

190         200         210         220         230         240
FYETKCNPMG  YTKEGCRG[D  [KRH]WNSQCRT  TQSYVRALTM  [SKKR]GWRF  IRIDTSCVCT
             B-2   B-4              B-3

LT[KRGR]
  B-5
```

FIGURE 1A

NEUROGENIC BRAIN-DERIVED NEUROTROPHIC FACTOR PEPTIDES

CROSS-REFERENCE TO RELATED APPLICATION

The present application is a divisional of U.S. application Ser. No. 13/939,352, filed on Jul. 11, 2013, which claimed priority to U.S. Provisional Application No. 61/670,325, filed on Jul. 11, 2012.

BACKGROUND OF THE INVENTION

1. Field of the Invention

The present invention relates to treatments for neurological disorders and, more particularly, to neurotrophic factor peptides.

2. Description of the Related Art

Brain derived neurotrophic factor (BDNF), a member of the neurotrophin family that also includes nerve growth factor (NGF), neurotrophin-3 (NT-3) and neurotrophin-4/5 (NT-4/5), promotes neuronal survival, differentiation, and synaptic function through the signaling of its receptor tropomyosin-related kinase-B (TrkB). Brain derived neurotrophic factor is of particular therapeutic interest because its expression levels are altered in many neurological disorders. A neurotrophic factor starvation, including NGF and BDNF deficiency, that begins in the early stages of Alzheimer disease (AD) and ultimately causes neuronal degeneration, cell death, and loss of cholinergic neurotransmission in the late stages of the disease has been reported. Additionally, the expression levels of BDNF are also reported to be reduced in Parkinson's disease (PD), depression, and stress. Conversely, autism spectrum disorders (ASDs) are characterized by an increase in BDNF levels. Thus, modulation of BDNF levels in these neurological disorders as a potential therapeutic approach is suggested.

Brain derived neurotrophic factor plays important roles in plasticity of several regions of the central nervous system (CNS) during development, adulthood, and ageing. The multiple roles of BDNF depend on functional and morphological changes, like protein phosphorylation, generation of new neurons, and cytoskeletal reorganization of dendritic spines. In hippocampal neurons, cyclic adenosine monophosphate (cAMP) controls BDNF-induced TrkB phosphorylation and dendritic spine formation by modulating the signaling and trafficking of TrkB.

Brain derived neurotrophic factor shares about 50% amino acid identities with NGF, NT-3 and NT-4/5. Each neurotrophin consists of a non-covalently-linked homodimer and contains a signal peptide following the initiation codon and a proregion containing an N-linked glycosylation site. Initially neurotrophins are produced as proneurotrophins (molecular weight—30 KDa), that are cleaved by enzymes such as prohormone convertases e.g. furin generating the mature neurotrophin (molecular weight of 14-26 KDa). Proneurotrophins have distinct biological activities and binding characteristics.

The immature form of BDNF is called proBDNF, and consists of 247 amino acids (in comparison with the mature form of BDNF that has 119 amino acids). This proneurotrophin binds a different receptor, known as low affinity p75NGFR, a member of the tumor necrosis factor (TNF) receptor super family and minimally binds Trk receptors. Brain derived neurotrophic factor and proBDNF are reported to have opposite effects. The activation of p75NGFR receptor can cause apoptosis in a variety of systems; instead, the activation of the TrkB receptor alone, as mentioned above, can promote differentiation, survival, and/or neuronal plasticity. Nevertheless, in physiological conditions neurons probably do not have high amounts of available extracellular proBDNF, because the endogenous proBDNF is rapidly converted to BDNF.

Pharmacologic modulation of BDNF levels has been suggested as a potential treatment strategy for human neurodegenerative diseases. A number of properties limit the therapeutic use of BDNF; the compound has a very short (less than 1 min) plasma half-life, and it has poor blood brain barrier (BBB) and intraparenchymal penetrations. Thus, the there is a need in the art for molecules, such as small peptides that could mimic or modulate the functions of BDNF, and have higher permeability and stability than BDNF itself. The general lack of success of neurotrophic factors in clinical trials (due to low stability in plasma and low permeability through the BBB) has led to the idea that low molecular weight neurotrophic factor mimetics can serve better as pharmacological agents.

However, the low plasma stability and low BBB permeability because of its moderately large size and ionic charge practically precludes the use of this neurotrophic factor as such for therapeutic usage, at least via peripheral administration. For instance, in a phase III clinical trial for the treatment of amyotrophic lateral sclerosis (ALS), a daily subcutaneous administration of BDNF offered no clinical benefit. Alternatively, direct administration of BDNF into the CNS to achieve beneficial neurotrophic effects may be a promising approach; however, there are also some considerations with this strategy that need to be taken into account. The CNS is composed of extremely delicate neural tissue sustained in a tightly controlled homeostatic environment, and direct intraventricular or intrathecal administration of a growth factor can cause undesirable effects. Direct administration of BDNF into the CNS has been reported to cause weight loss, dysaesthesias (impairment of sensation), and in some cases, pain. Direct administration into CNS can be a better alternative if effective concentrations of the neurotrophic factor can be achieved at precise sites of degenerating neurons, while limiting the spread to distant sites to avoid undesirable effects.

One method to attain this can be gene delivery via adeno-associated viral vectors (AAVs). However, this approach is now in evaluation, and it requires additional improvements to guaranty the safety of the patients. Other alternatives include non-pharmacologic approaches for BDNF augmentation such as exercise and diet modulation. Physical exercise increases BDNF levels in the hippocampus and the cortex, and may enhance learning and memory, synaptic plasticity, and neurogenesis. Caloric restriction also affects the levels of BDNF. However, changes in BDNF expression levels due to exercise or caloric restriction are low as compared with the direct administration of the neurotrophic factor by infusion. Epigenetic modulation of gene transcription, as an alternative approach, can be achieved through direct methylation of DNA or by post-translational modification of histones, which can either repress or promote gene transcription. Fear conditioning has been shown to differentially regulate the expression of BDNF mRNAs, following BDNF DNA methylation. Drugs that are able to increase BDNF levels in the brain include antidepressants, e.g., lithium, that is able to increase 30% BDNF concentrations in serum, and ampakines that increase BDNF and improve stabilization of LTP and long-term memory in a mouse model of Huntington's disease. Whether these drugs induce sufficient changes in BDNF levels to be useful for human diseases remains to be determined. Also remaining to be evaluated are the mechanisms that these drugs employ to modulate BDNF expression, since most of them can also activate alternative cellular signaling pathways, generating a complex mechanism of action.

In order to exploit the therapeutic value of BDNF, some peptide mimetics have been identified. For the selection of the group of molecules, in silico screening (computational modeling) with a BDNF loop-domain pharmacophore was, followed by in vitro screening in mouse fetal hippocampal neurons. These small molecules (LM22A1 to 4) showed neurotrophic activity specific to TrkB versus other Trk family members (Massa, Yang et al. 2010). However, these molecules were not peptides in chemical structure, so they may have disadvantages such as toxicity or low solubility that could hinder their development as clinical drugs.

BRIEF SUMMARY OF THE INVENTION

In accordance with the foregoing objects and advantages, the present invention provides five different tetra peptides (peptides B-1 to B-5) corresponding to different active regions of BDNF, namely $BNDF_{6-9}$ (Peptide BDNF-1) (SEQ ID NO: 1), $BDNF_{71-74}$ (Peptide BNDF-2) (SEQ ID NO: 2), $BDNF_{94-97}$ (Peptide BDNF-3) (SEQ ID NO: 3), $BDNF_{72-75}$ (Peptide BDNF-4) (SEQ ID NO: 4), and $BDNF_{115-118}$ (Peptide BDNF-5) (SEQ ID NO: 5). As the levels of BDNF are down regulated in Alzheimer's disease (AD), Parkinson's disease (PD), depression, stress, and anxiety; and, conversely, the levels of this neurotrophin are increased in autism spectrum disorders, modulating the levels of BDNF according to the present invention may be a potential therapeutic approach for these and other nervous system pathologies.

The five tetra peptides of the present invention were found to be non-toxic, and they induced the expression of neuronal markers in mouse embryonic day 18 (E18) primary hippocampal neuronal cultures. Additionally, peptide B-5 induced the expression of BDNF and its receptor TrkB, suggesting a positive feedback mechanism. The BDNF peptides induced only a moderate activation (phosphorylation at Tyr 706) of the Trk B receptor which could be blocked by the Trk's inhibitor, K252a. Peptide B-3, when combined with BDNF, potentiated the survival effect of this neurotrophin on $H_2O_2$-treated E18 hippocampal cells, acting as a partial agonist. Peptides B-3 and B-5 were also found to work as partial antagonists, competing with BDNF, to activate the TrkB receptor in a dose-dependent manner. Taken together, these results suggest that the described BDNF tetra peptides are neurotrophic, can modulate BDNF signaling in a partial agonist/antagonist way, and offer a novel therapeutic approach to neural pathologies where BDNF levels are dysregulated.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 1A is a graphical representation of the amino acid sequence of human BDNF (SEQ ID NO: 6), where the signal peptide (18 amino acids, positions 1-18) is shown in green, the propeptide (110 amino acids, positions 19-128) is shown in blue, and the BDNF sequence, (119 amino acids, positions 129-247, molecular weight 26 kDa) is shown in black, and the sequences of the five tetra peptides of the present invention (B-1 to B-5) are boxed in red squares.

Figure 2A:
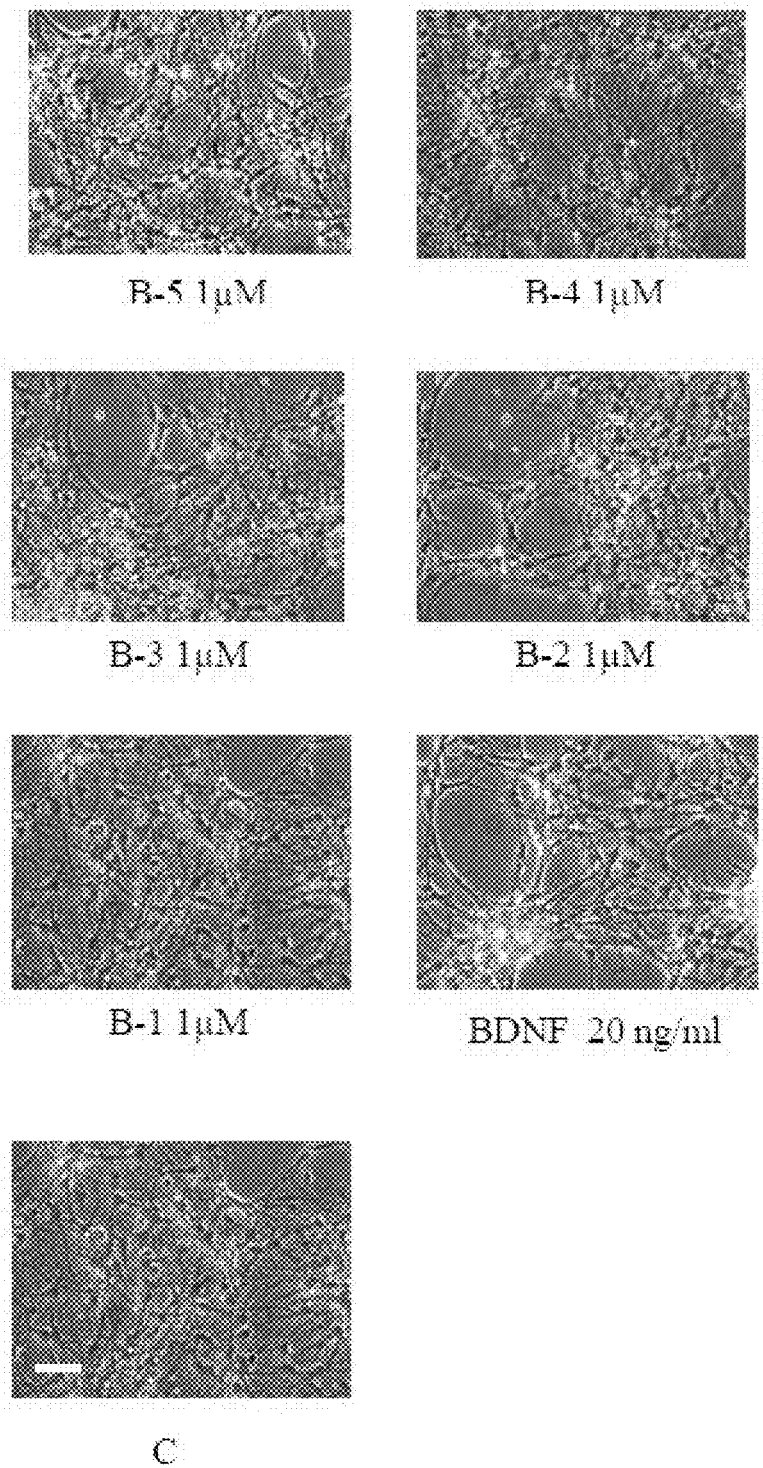
FIG. 2A is a series of image phase contrast photomicrographs of hippocampal neurons vehicle-treated or treated with BDNF (20 ng/ml) or the indicated peptides (at 1 μM) for five days, where the scale bar represents 20 μm.
Figure 2B:
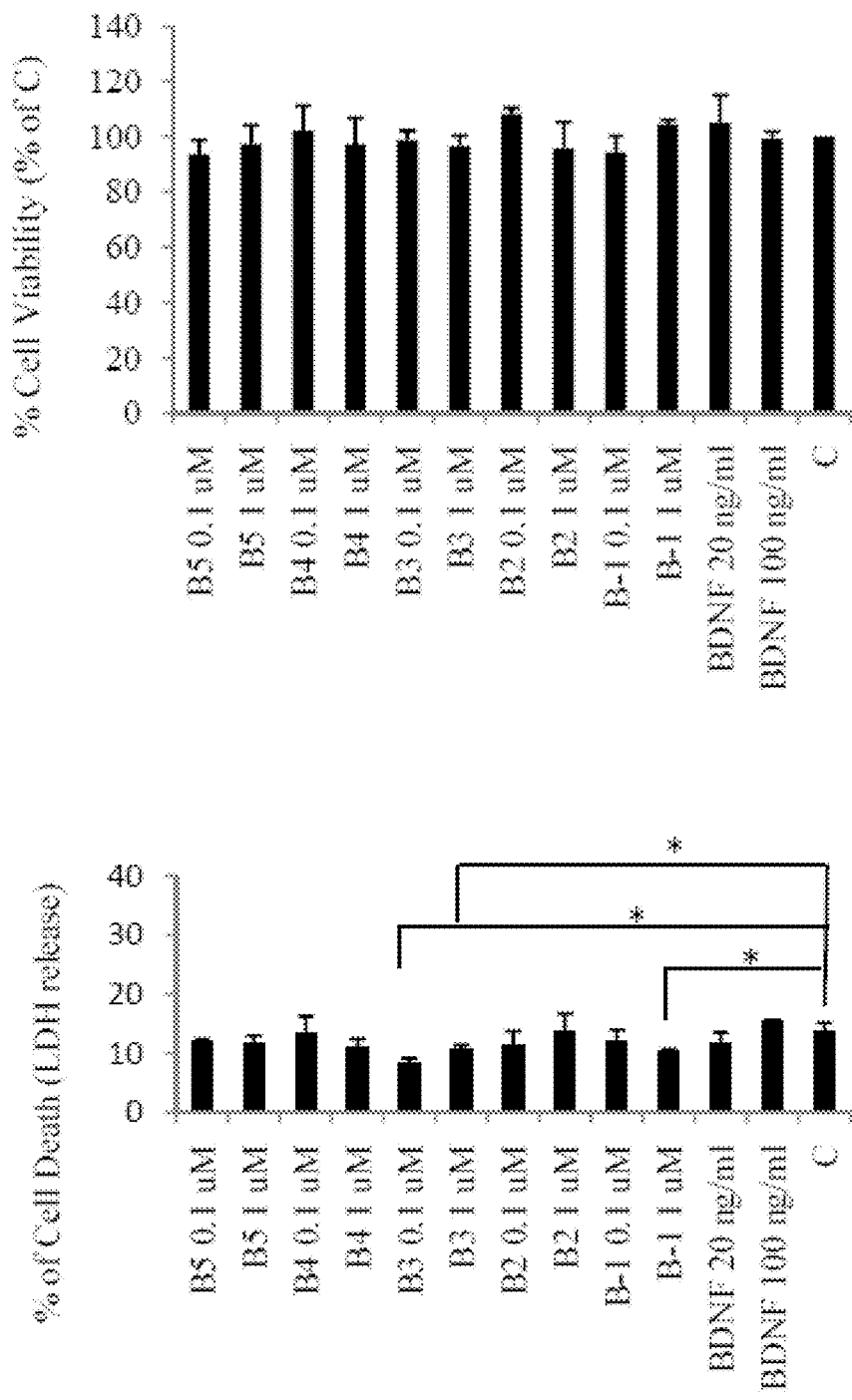

FIG. 2B is a chart illustrating the effect of BDNF peptides on neuronal survival via a lactate dehydrogenase (LDH) assay showing the percentages of cell viability and cell death after five days of treatment with the peptides (at 0.1 or 1 μM) or BDNF (at 20 and 100 ng/ml; 0.79 and 3.95 nM respectively), where counts were normalized to survival achieved with vehicle treatment for 5 days (control, C), values for each concentration were derived from 3 independent experiments, and *$p<0.05$, Student's t test.

Figure 3A:
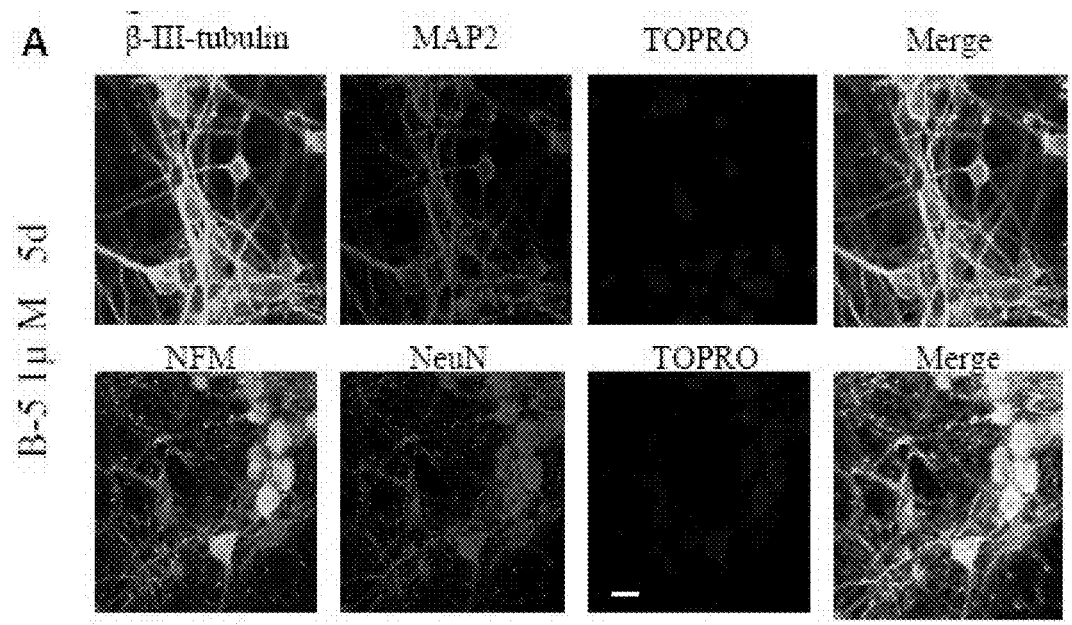
Figure 3B:
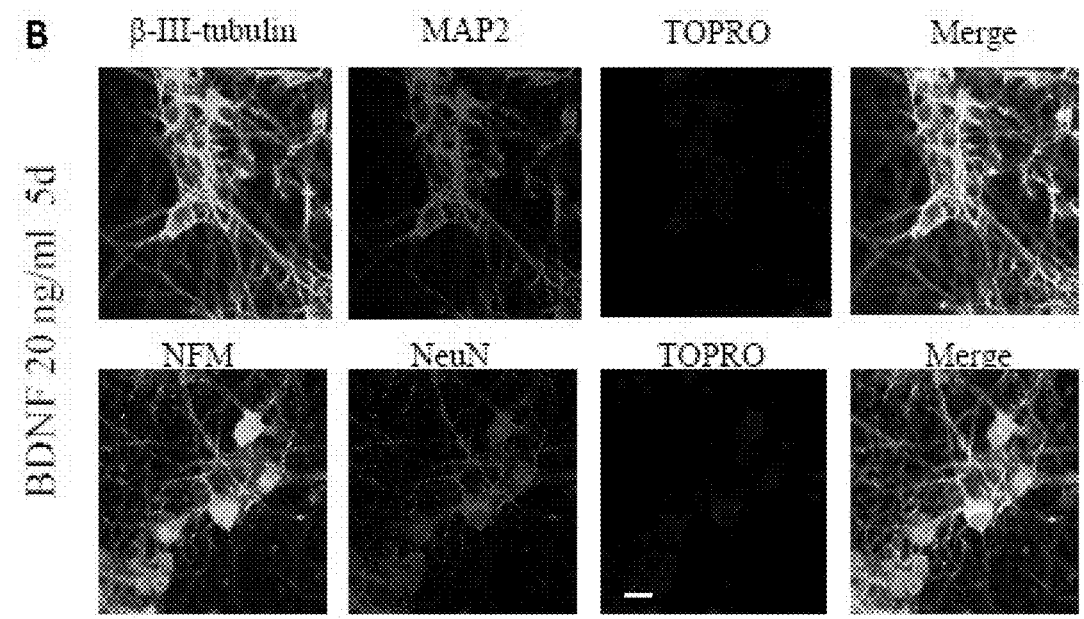
Figure 3C:
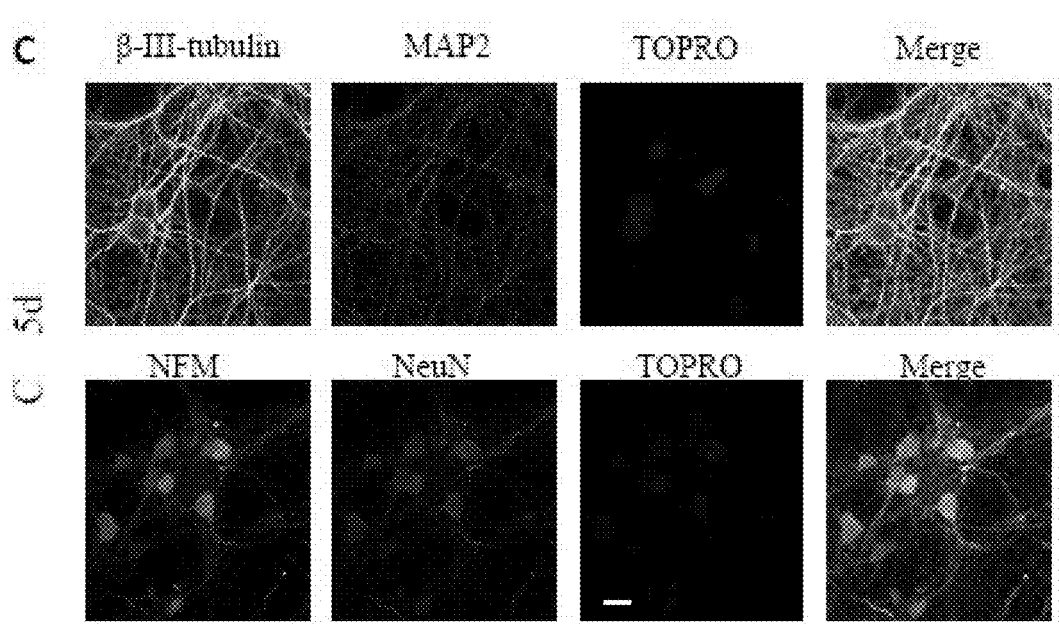

FIG. 3A through 3C are confocal images showing that BDNF peptides B-5, B-4, and B-3 are neurogenic and neurotrophic, by illustrating double immunolabelling of 0-III-tubulin (green) and MAP2 (red) and NFM (green) and NeuN (red) in cells treated for 5 days with (A) Peptide B-5 at 1 μM, (B) with BDNF, 20 ng/ml (0.79 nM) for 5 days, and (C) vehicle only (control, C). TOPRO-3 (blue) was used to stain the nuclei and the magnification bar=10 μm.

Figure 3D:
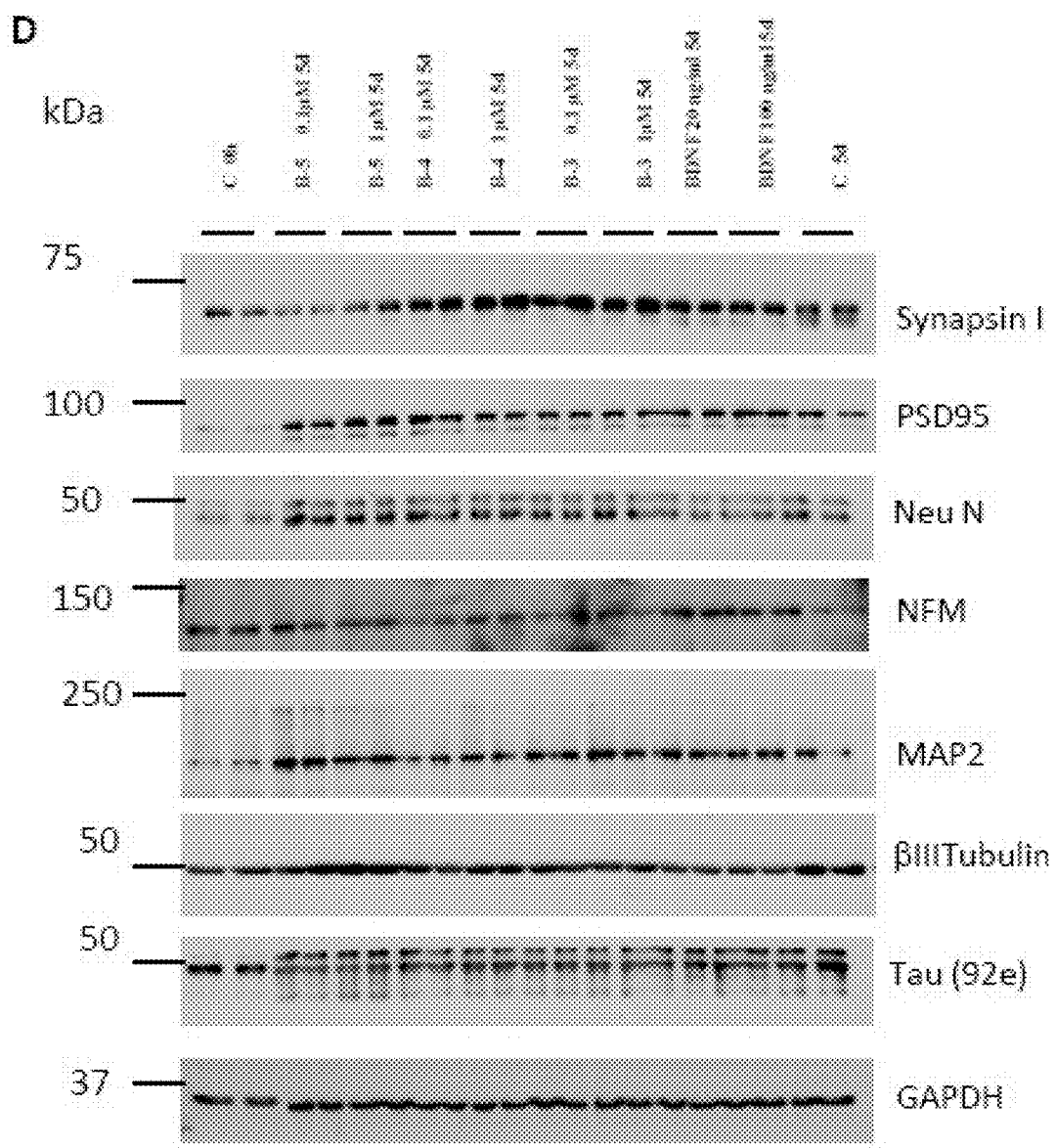
Figure 3E:
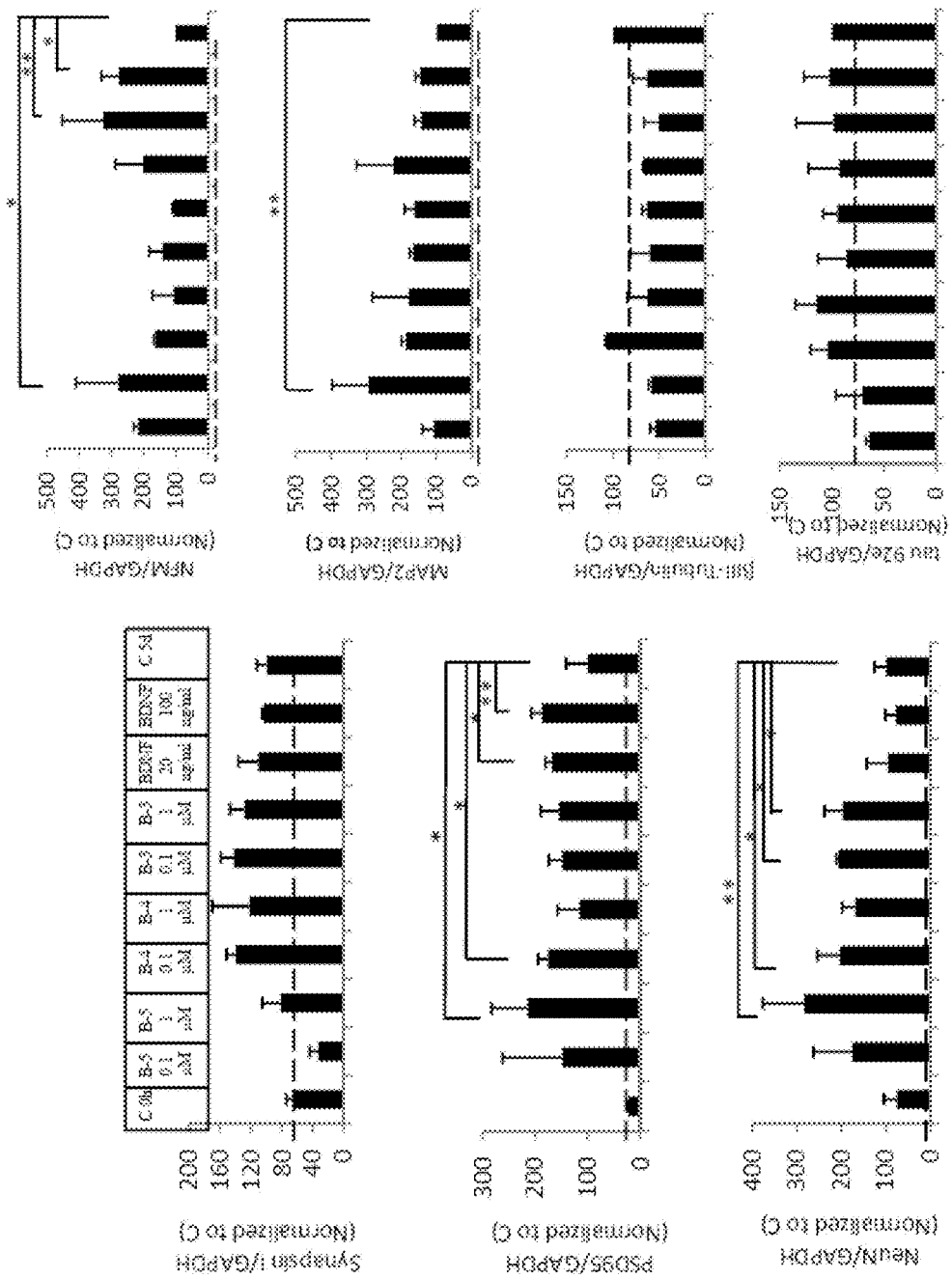

FIGS. 3D and 3E show that the BDNF peptides (B-3, B-4, and B-5) induce the expression of neuronal markers in E18 primary hippocampal neurons, where FIG. 3D is a series of representative Western blots showing an increase in the expression of the neuronal markers PSD95, NeuN, NFM, and MAP-2 in cells treated with the peptides (B-3, B-4 and B-5) at concentrations of 0.1 μM and 1 μM or BDNF at concentrations of 20 or 100 ng/ml (0.79 or 3.95 nM respectively) with GPADH was used as a loading control, and FIG. 3E is a graph of the quantification of the Western blots of neuronal markers shown in FIG. 3D, where the integrated density value of the bands in Western blots was determined using densitometry (Fuji software, Multi Gauge, Version 3.0), and data was normalized to GAPDH and to control (medium treated cells for 5 days, C 5d). Data are shown as mean±standard deviation, n=3. 10% SDS-PAGE gels, and *$p<0.05$, **$p<0.001$ in a one-way ANOVA/post-hoc test/Student's t test.

Figure 4A:
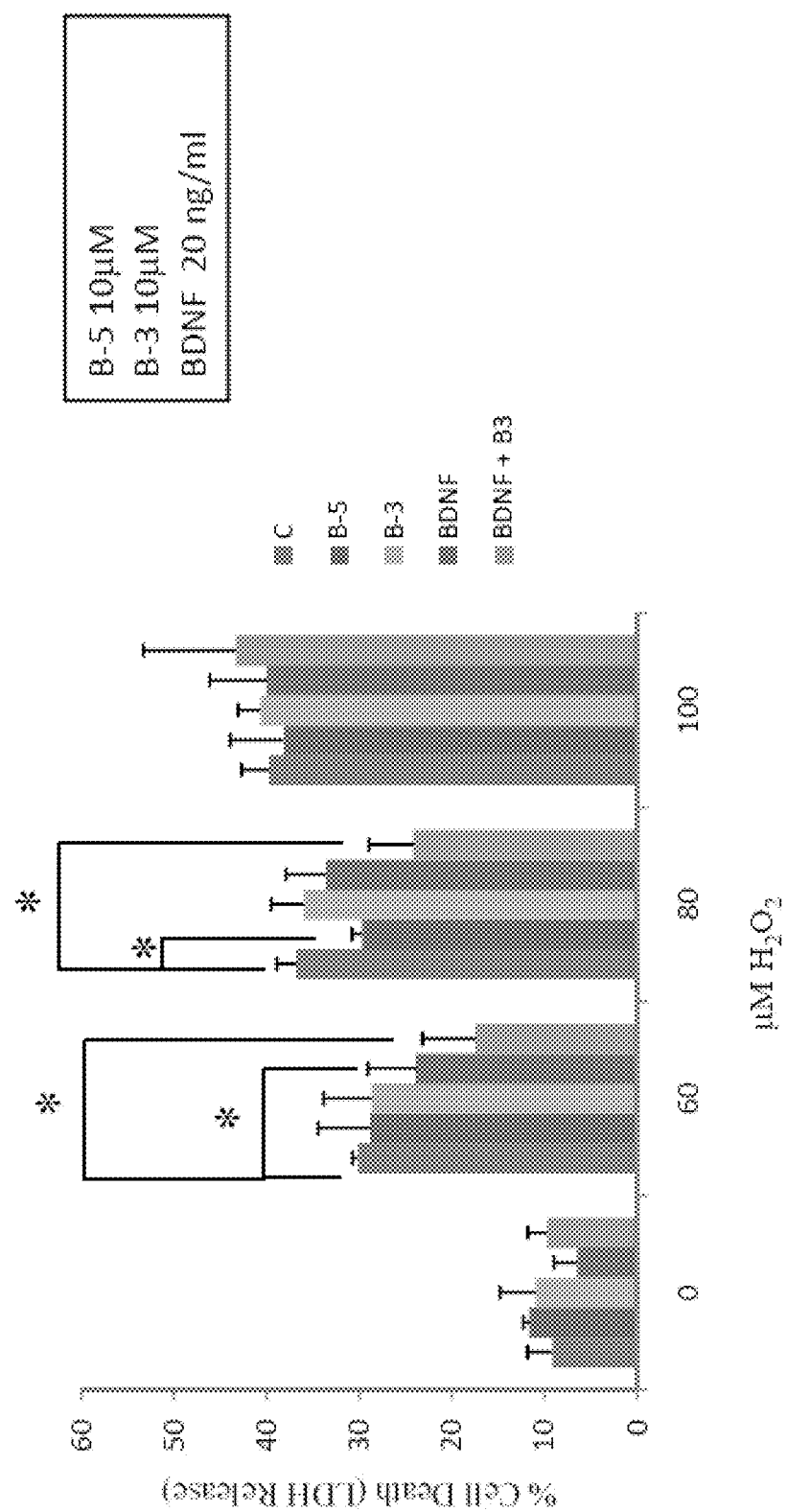
Figure 4B:
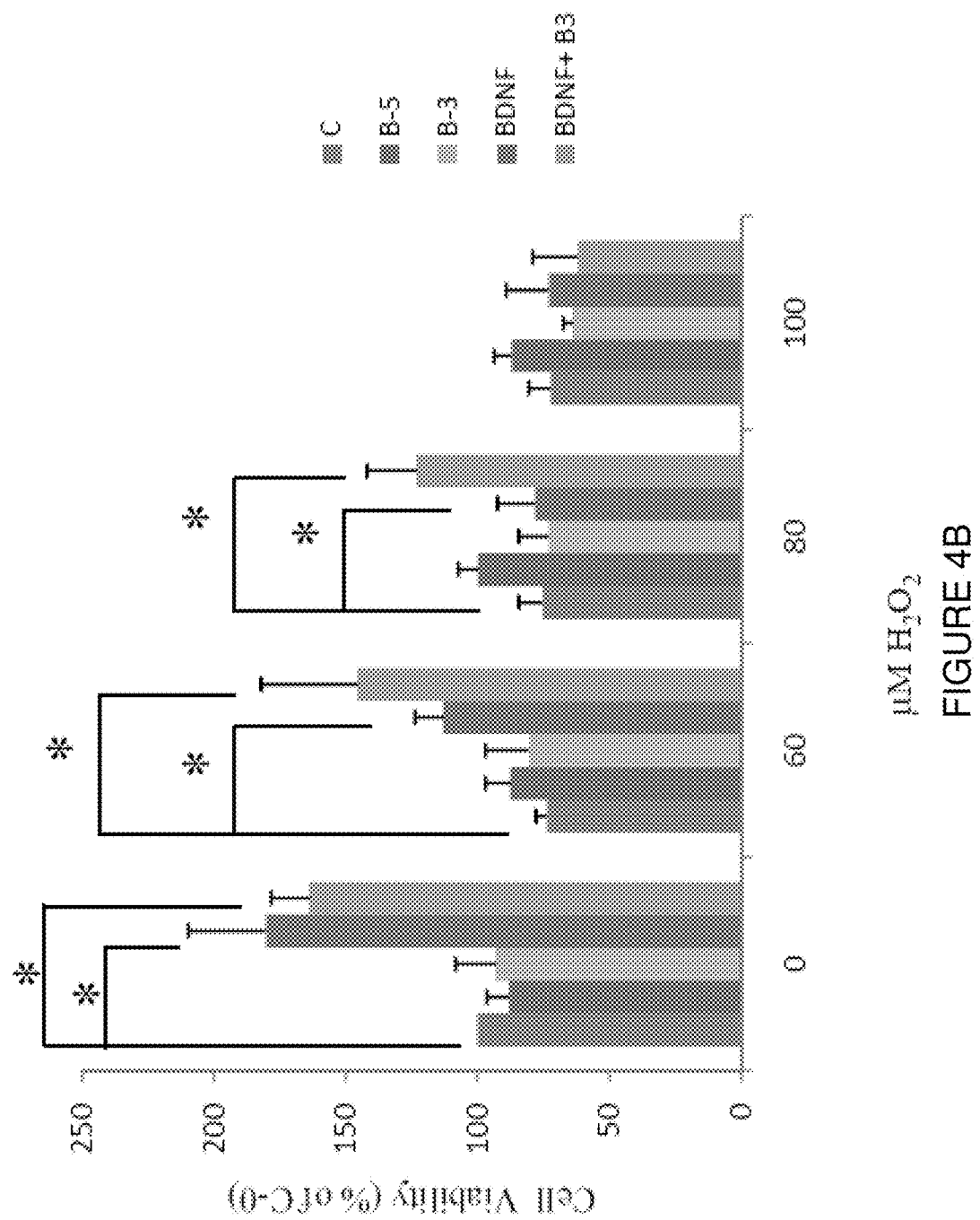

FIGS. 4A and 4B are charts showing the BDNF peptides potentiate the effect of BDNF in rescuing $H_2O_2$-induced neurotoxicity, where FIG. 4A is a graph of an LDH cytotoxicity assay showing the percentage of cell death in hippocampal cells treated with increasing concentrations of $H_2O_2$ i.e. 0, 60, 80, and 100 μM for 6 h, and then after changing the medium, exposed to B-5, B-3, BDNF or BDNF+B-3 for 24 h. Peptide B-5 significantly reduced cell death caused by 80 μM $H_2O_2$ and Peptide B-3 significantly potentiated the neuroprotective effect of BDNF. FIG. 4B is a chart of the percent viability of hippocampal cells by LDH assay, where the cells were treated in the same way as in A. Peptide B-3 significantly increased the viability when combined with BDNF in cells not treated or treated with 60 or 80 μM of $H_2O_2$. Data were normalized to control (vehicle treated cells). * $p<0.05$, ANOVA and/or Student's t test, n=3.

Figure 5A:
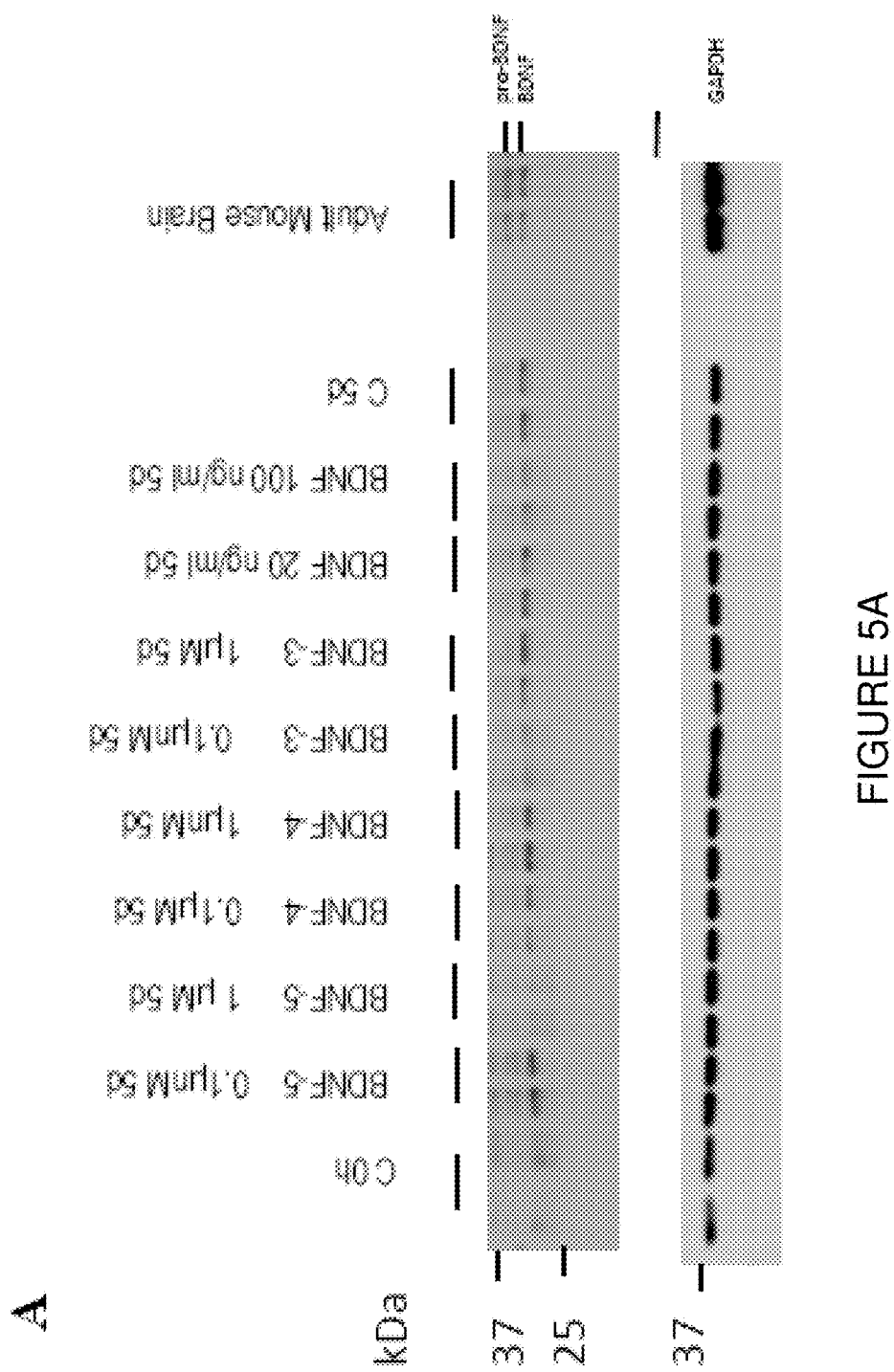

FIG. 5A is a Western blot analysis of cells treated with peptides B-5, B-4 and B-3, or with BDNF, or vehicle for five days, showing an increase in BDNF expression in cells treated with the peptides, with a sample of adult mouse brain included as a control for the migration of the bands corresponding to proBDNF and BDNF.

Figure 5B:
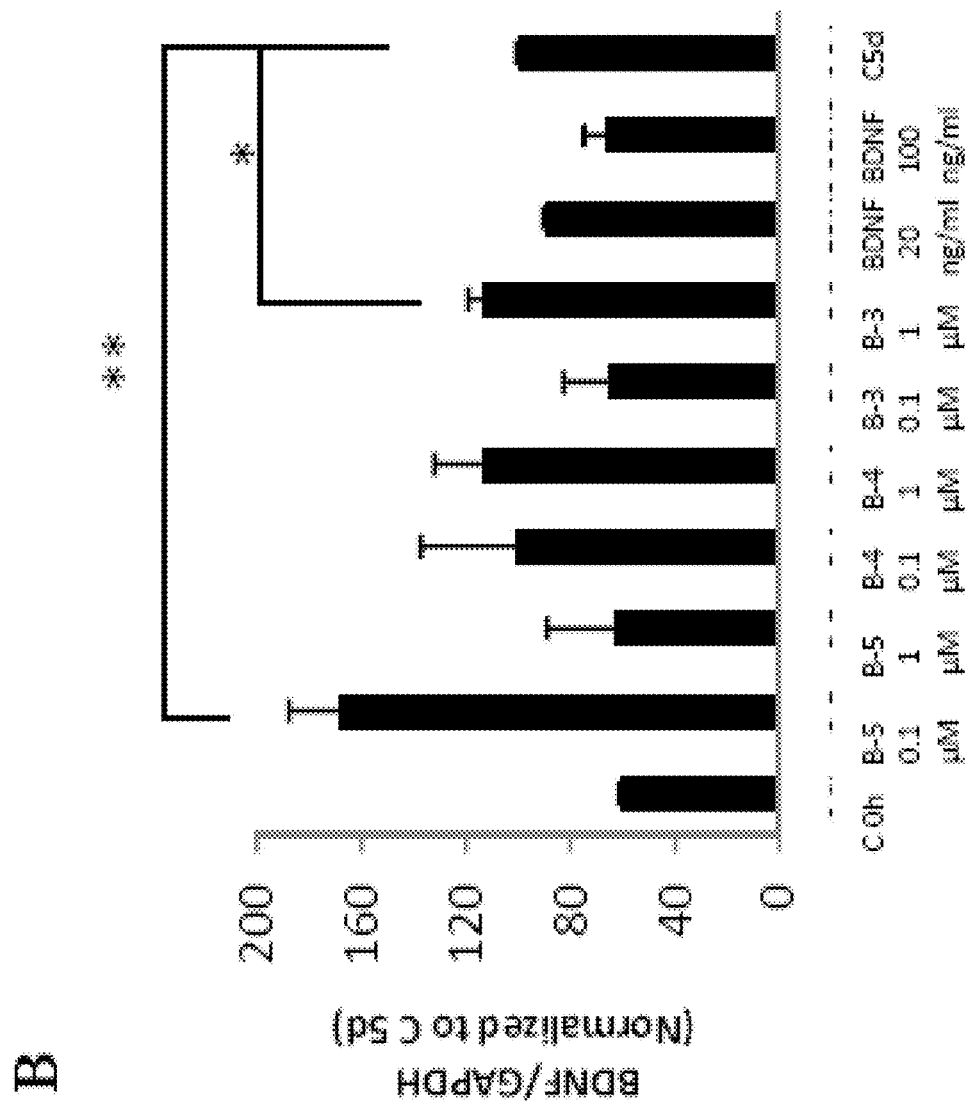

FIG. 5B is a graph of the densitometric quantitation of the Western blots developed with antiBDNF, where data was normalized to GAPDH as loading control and then to 5 days control vehicle treated cells, C 5d.

Figure 5C:
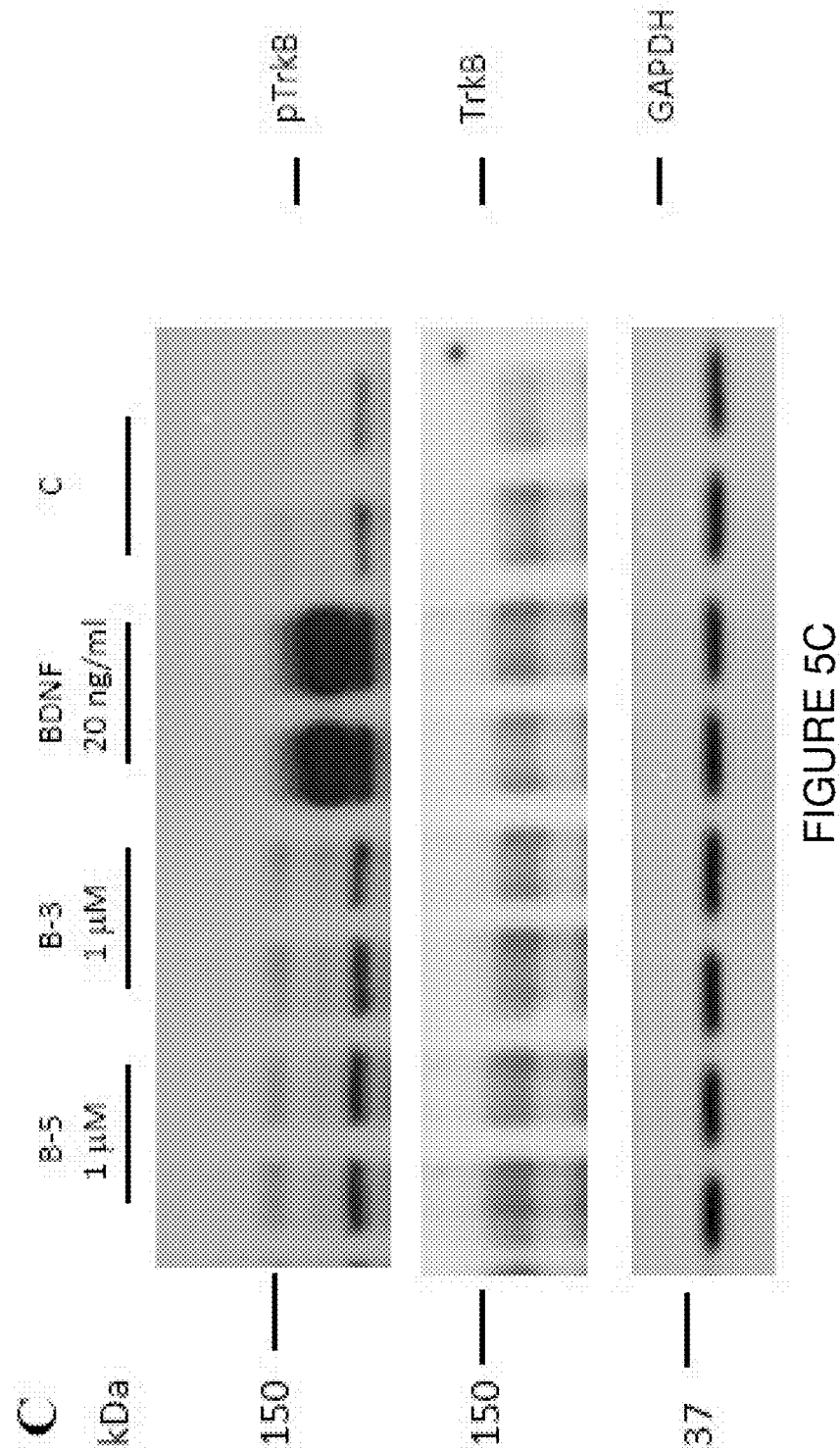

FIG. 5C is a Western blot showing phosphorylation of TrkB at Tyr 706 on treatment with Peptide B-5 (1 µM), Peptide B-3 (1 µM) or BDNF (20 ng/ml, 0.79 nM) for 1 h as compared to control treated cells, C, where lower blots show the levels of TrkB receptor and the levels of GAPDH as a loading control.

Figure 5D:
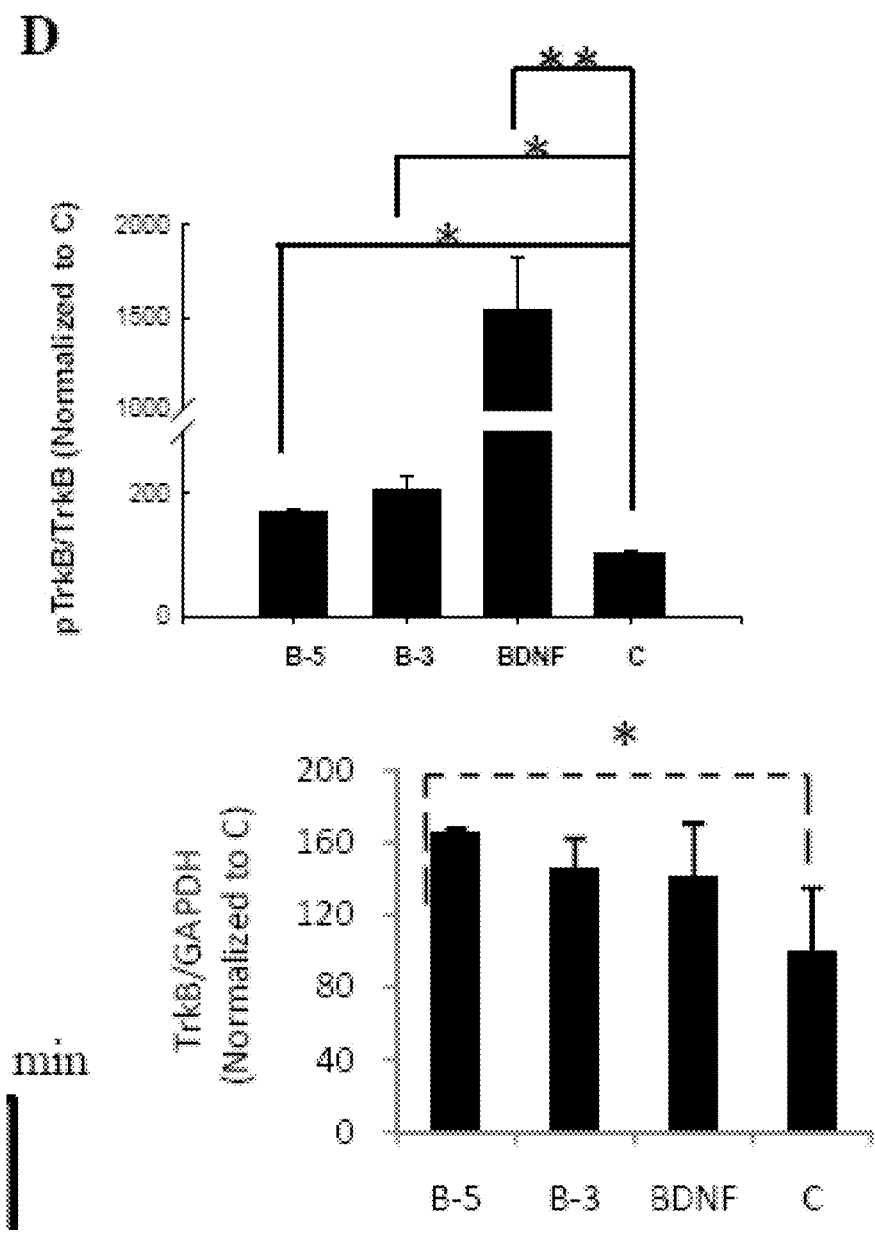

FIG. 5D is a graph of the densitometric analysis of the Western-blots for pTrkB normalized to TrkB, and TrkB normalized to GAPDH, where Control was taken as a 100 percent in each case, where the dashed line denotes that B-5 induction of TrkB expression almost approaches the significance (p=0.057, one-way ANOVA).

Figure 5E:
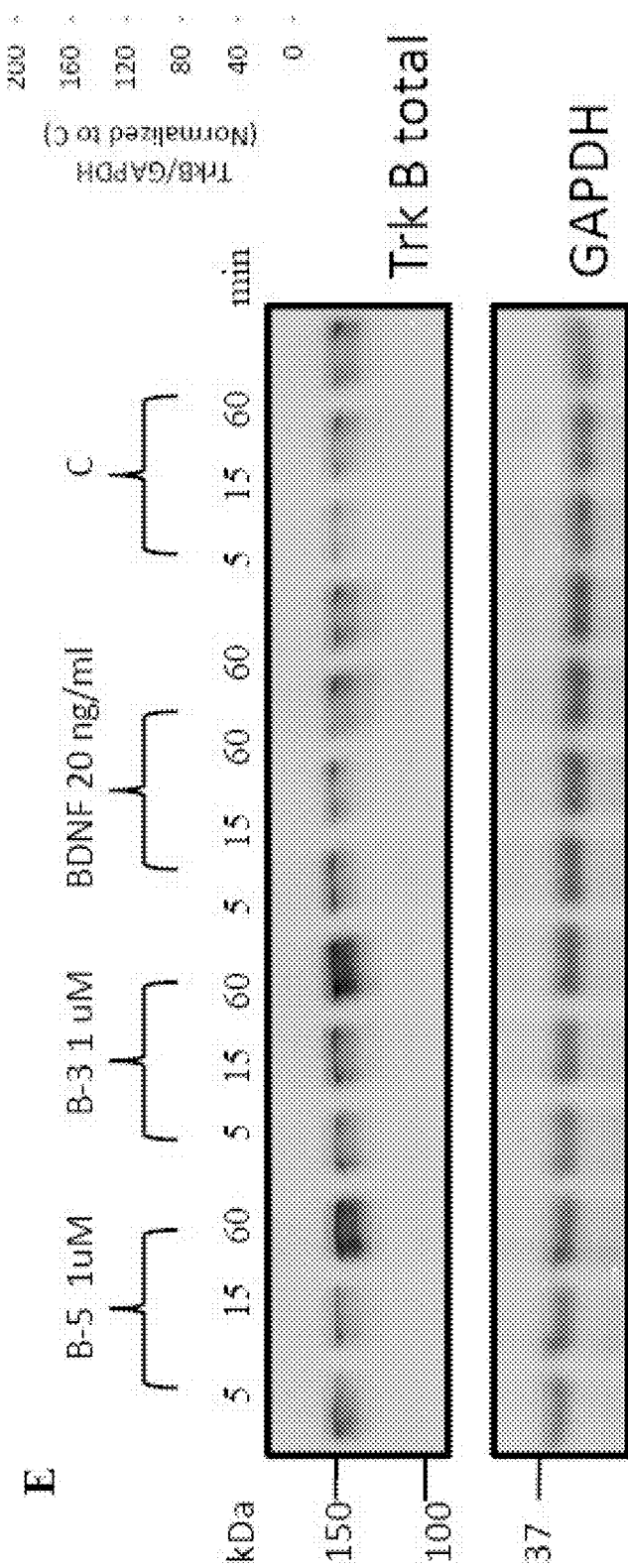

FIG. 5E is Western blot of total TrkB, and GAPDH included as a loading control showing BDNF peptides (B-5 and B-3) increasing the expression of TrkB in TrkB stably-expressing NIH-3T3 fibroblast cells, as a function of time, where cells were treated for 5, 15 or 60 min with B-5 (1 µM), B-3 (1 µM), BDNF (20 ng/ml), or vehicle only (Control, C).

Figure 5F:
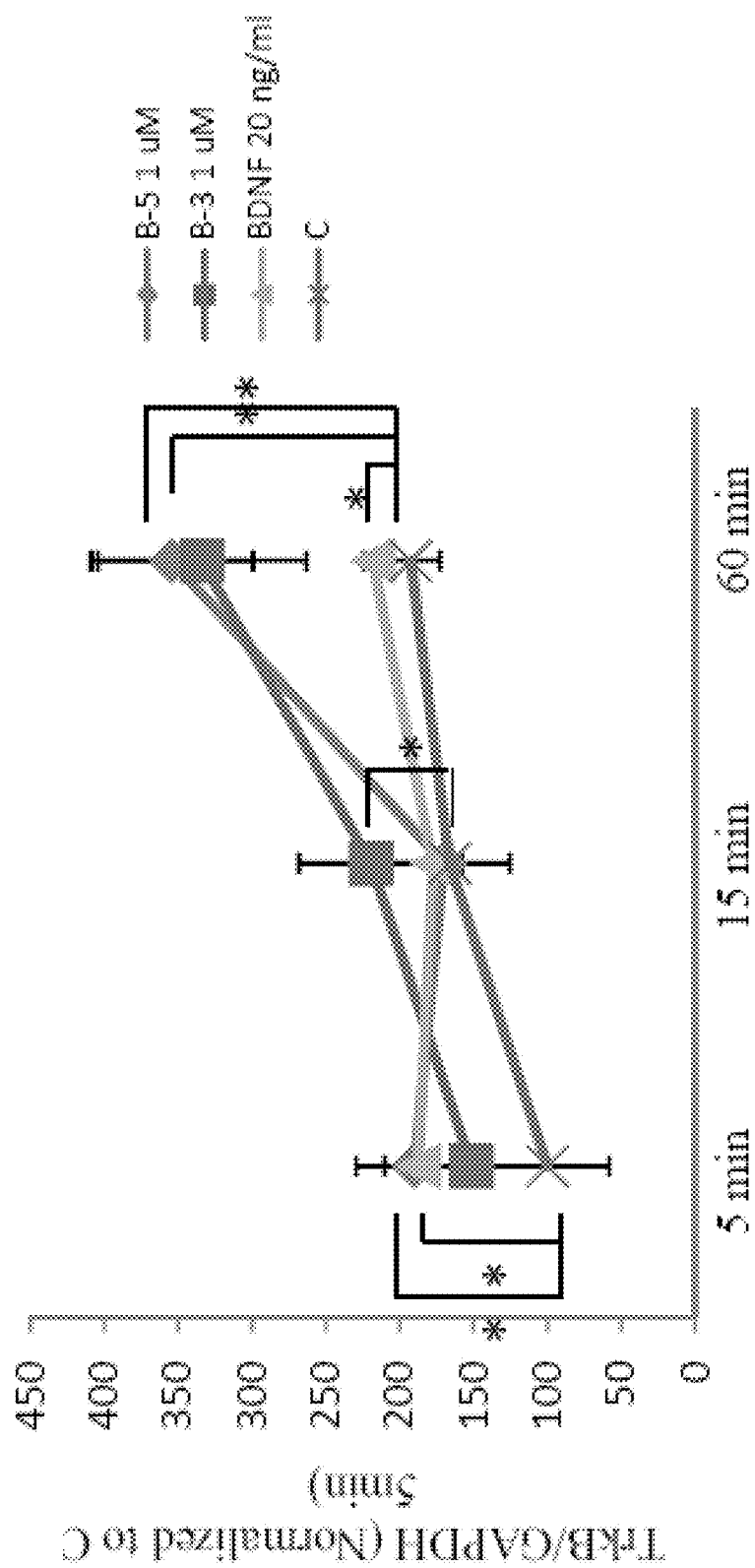

FIG. 5F is a graph of the densitometric quantitation of the Western blots for TrkB normalized to GAPDH, where data are shown as mean±standard deviation, n=3 and *p<0.05, **p<0.001, one-way ANOVA/post-hoc test/Student's t test.

Figure 6A:
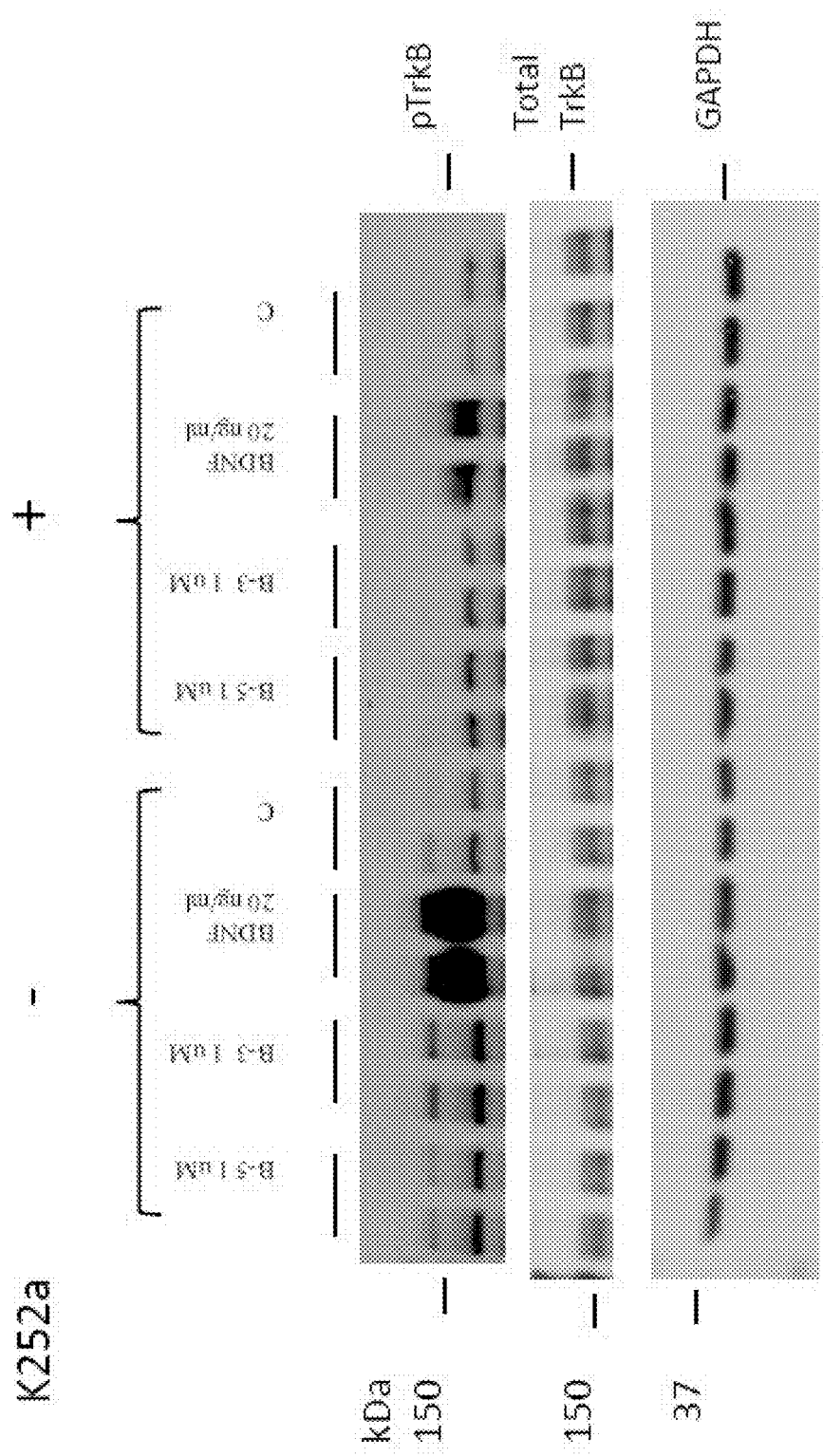

FIG. 6A is a Western blot of pTrkB (Tyr 706), total TrkB and GAPDH included as loading control showing that activation of the TrkB receptor by BDNF peptides B-5 and B-3 can be blocked by the TrkB inhibitor, K252a, where cells were pretreated with or without K252a for 1 h and then exposed to Peptide B-5 or Peptide B-3 at 1 µM or 20 ng/ml BDNF for 5 min.

Figure 6B:
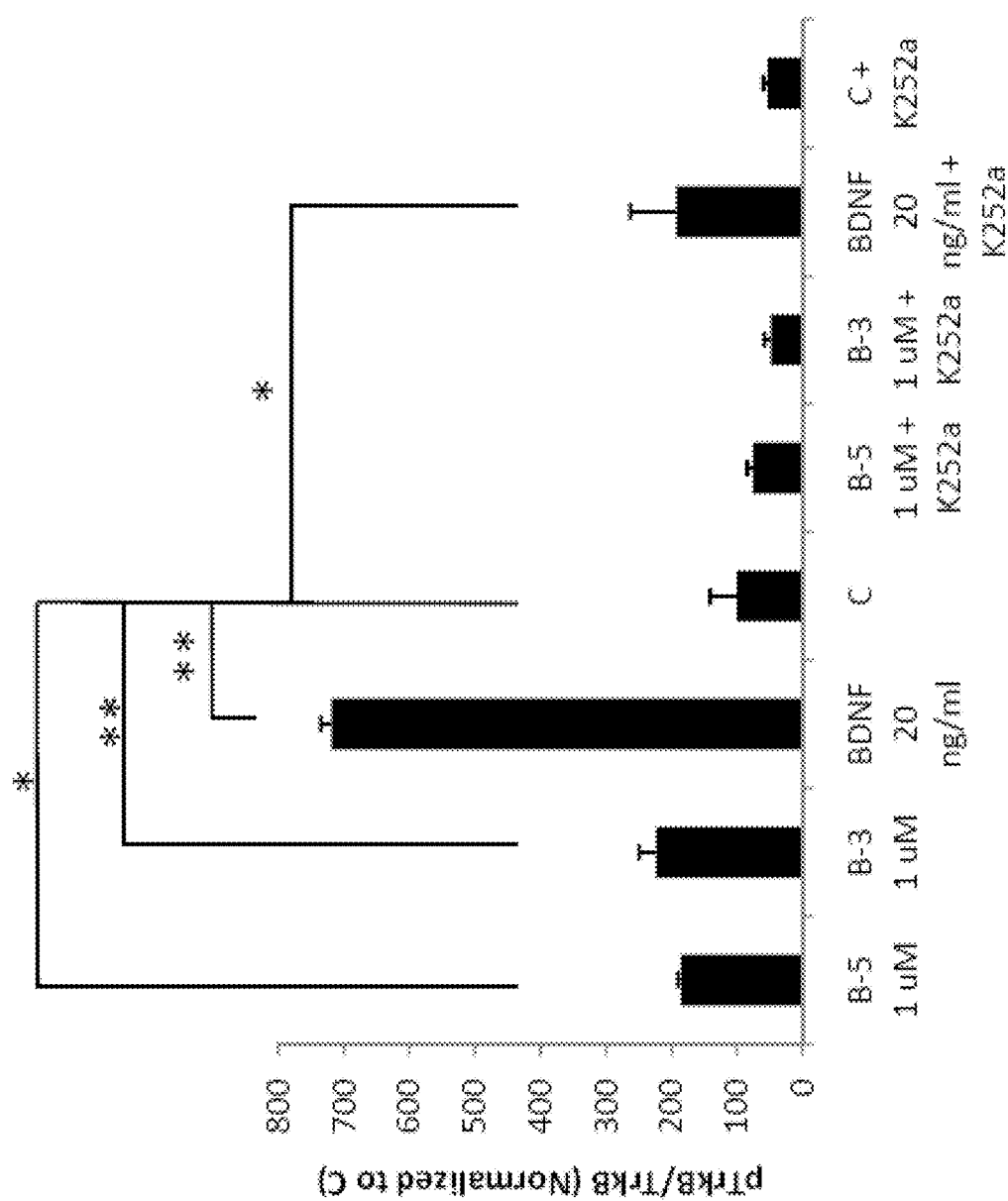

FIG. 6B is a graph of the densitometric quantitation of the Western-blots for pTrkB normalized to TrkB, where data are shown as mean±standard deviation, n=3, *p<0.05, **p<0.001, and one-way ANOVA.

Figure 7A:
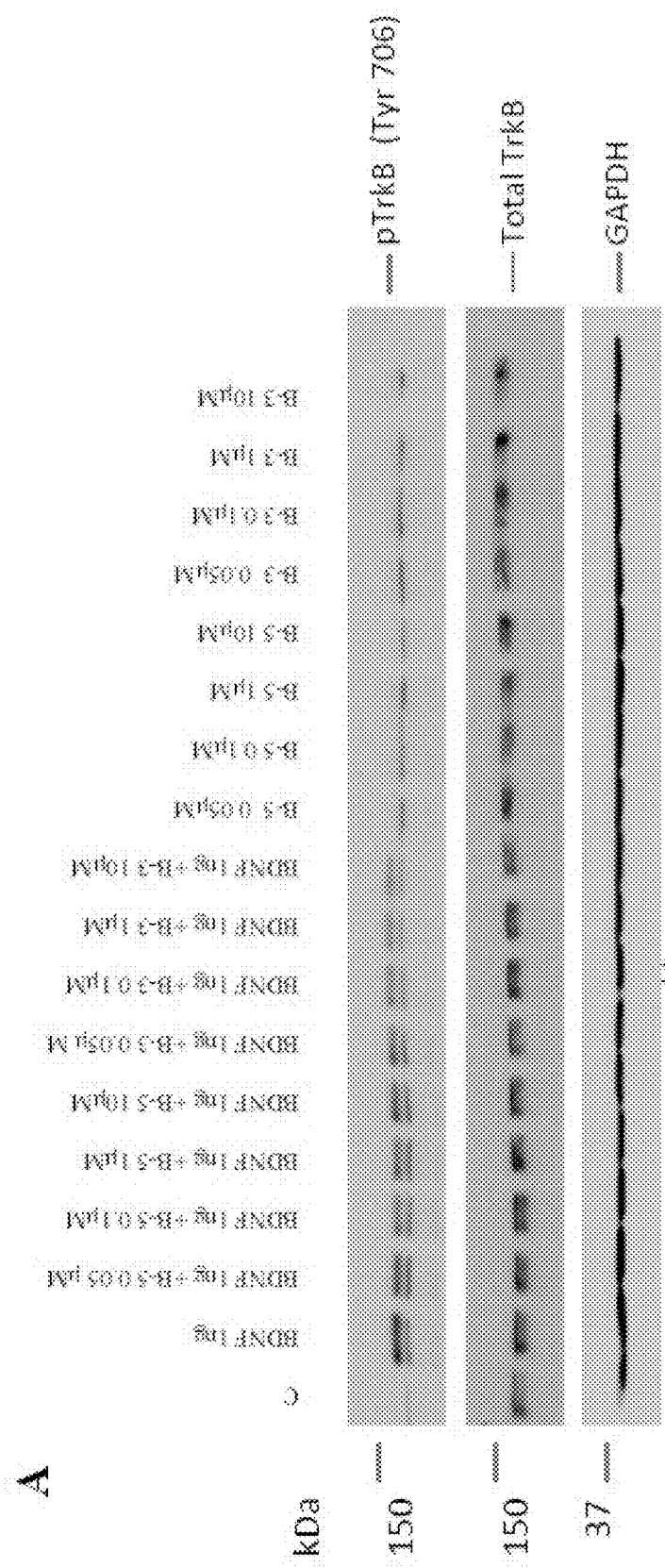

FIG. 7A is a Western blot of pTrkB (Tyr 706) and of total TrkB with GAPDH included as a loading control showing that the BDNF peptides act as partial agonists and antagonists of BDNF with competition experiments showing inhibition of the activation (pTrkB) of the TrkB receptor when the TrkB receptor stably expressing NIH-3T3 fibroblasts were treated with increasing concentrations of peptides B-5 or B-3 in the presence or absence of BDNF for 15 min.

Figure 7B:
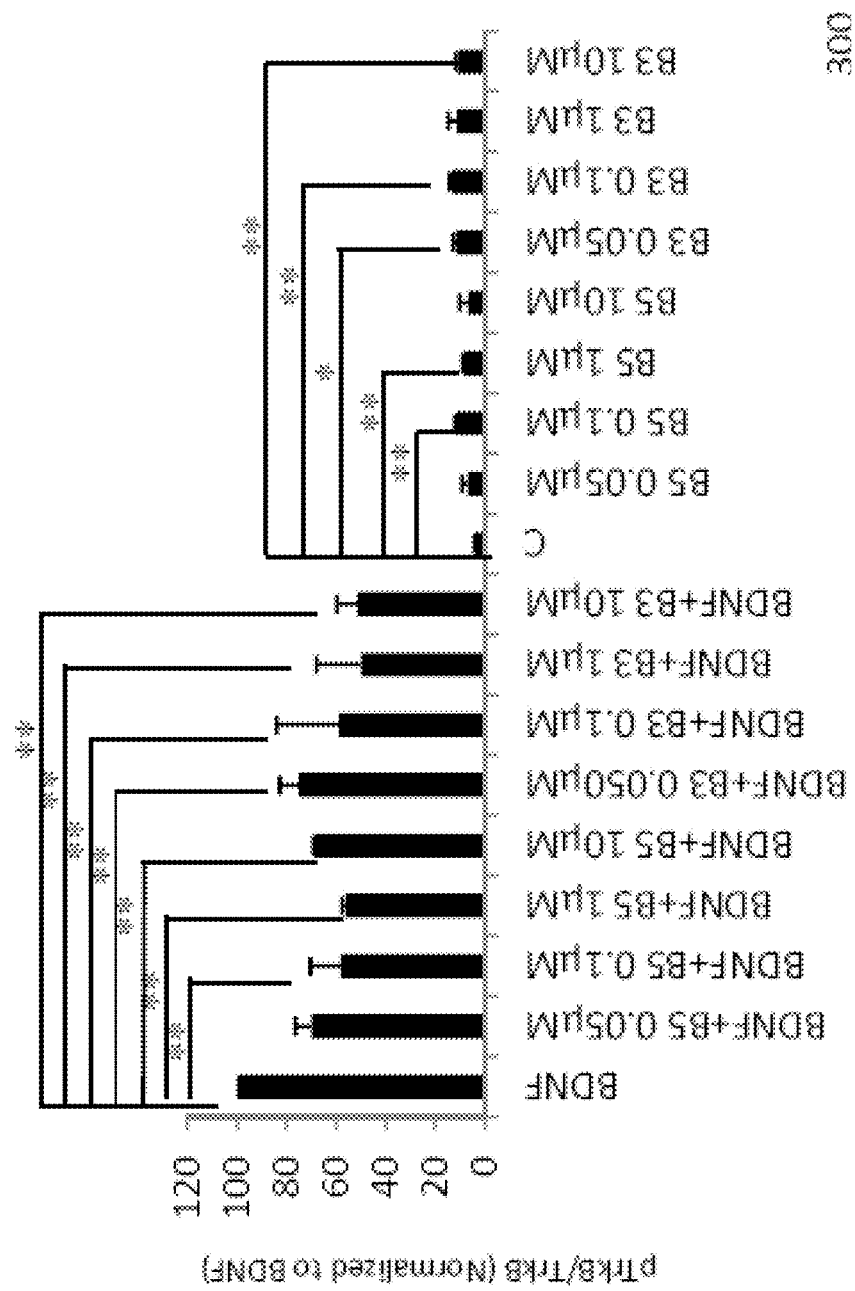
Figure 7C:
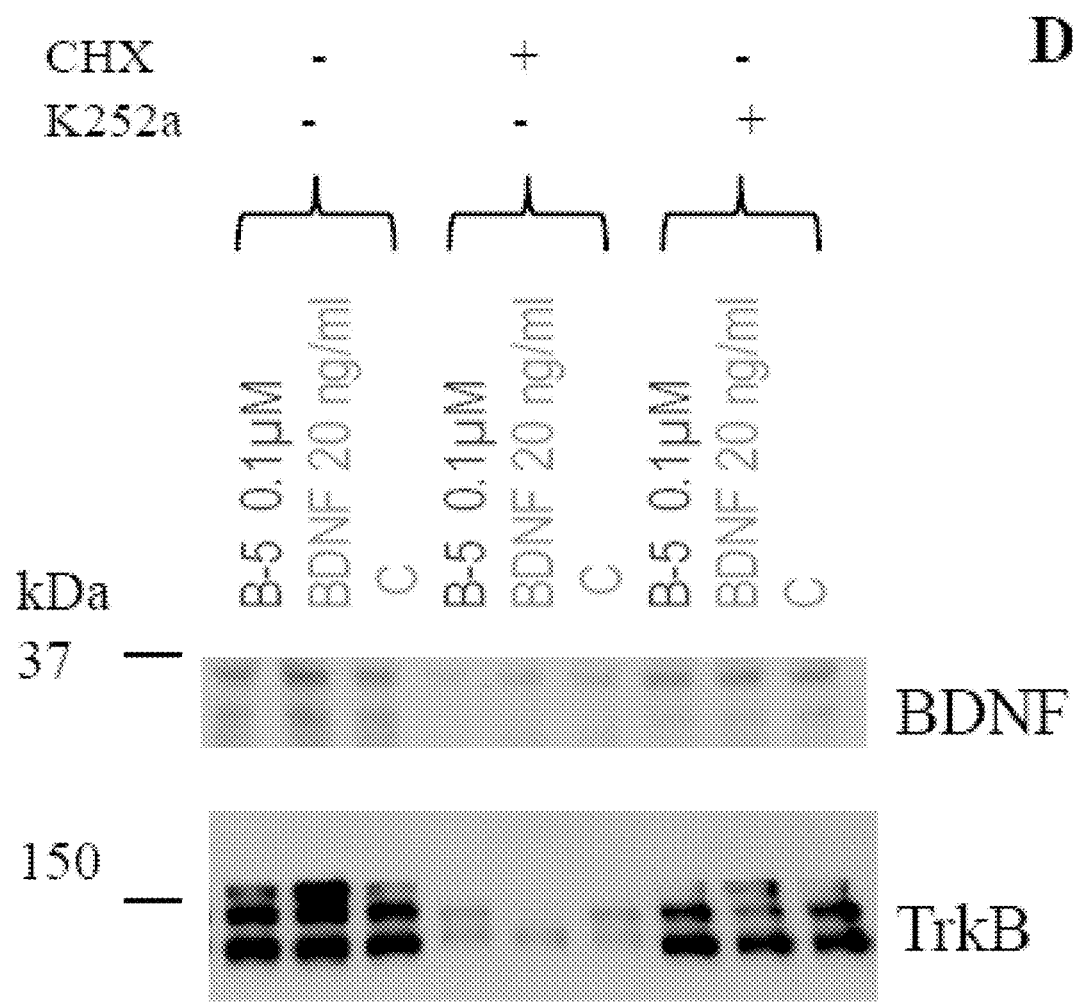

FIG. 7B is a graph of the densitometric quantitation of the Western blots for pTrkB normalized to TrkB (after normalizing TrkB to GAPDH) and shown as a percentage of BDNF;

FIG. 7C is a Western blot of BDNF, and total TrkB, of hippocampal cells treated with 0.1 µM peptide B-5 or 20 ng/ml BDNF or vehicle treated, and when indicated, also pretreated with CHX or K252a showing the increase in expression of BDNF in primary hippocampal cells caused by BDNF peptides or BDNF after two days of treatment can be blocked by pre-exposure (1 h before adding the peptides) to protein synthesis inhibitor, cycloheximide (CHX) or to TrkB inhibitor, K252a.

Figure 7D:
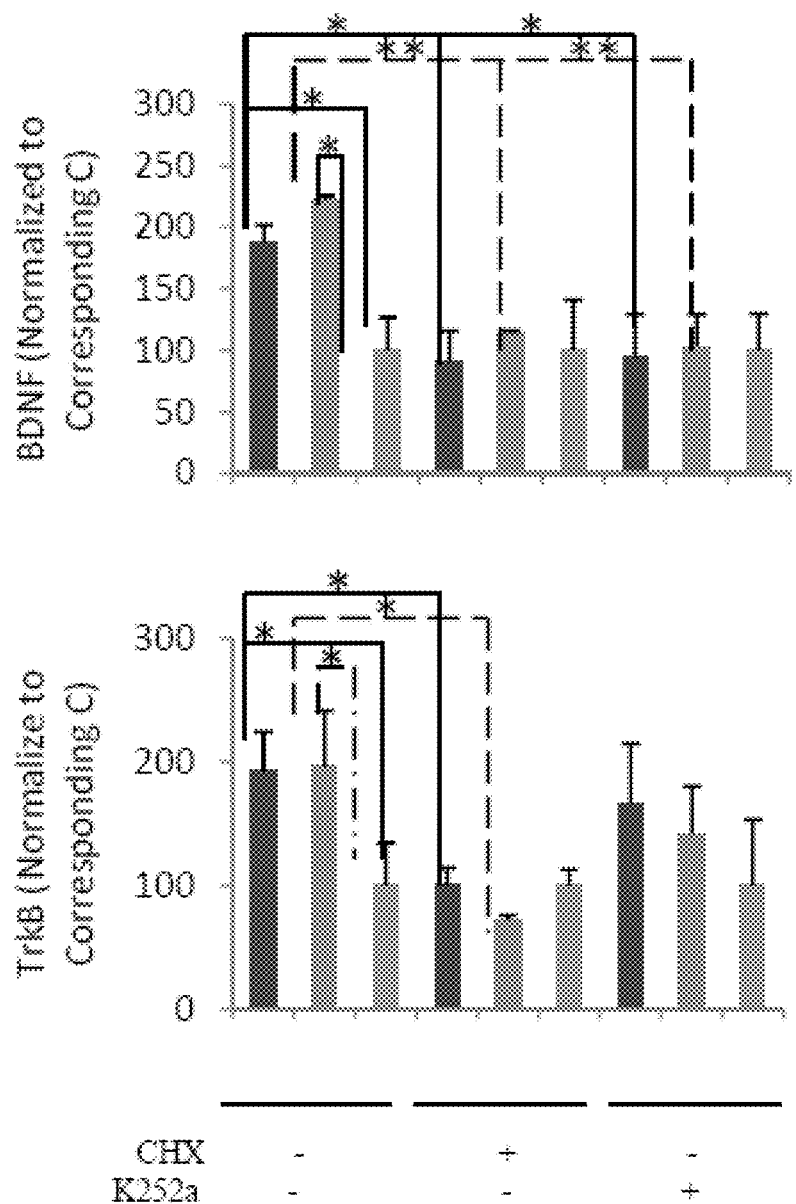

FIG. 7D is a graph of the densitometric quantitation of the Western-blots for BDNF and TrkB normalized to the corresponding control cells (control, C) in each condition, where data are shown as mean±standard deviation, n=3, *p<0.05, **p<0.001, and one-way ANOVA/post-hoc test/Student's t test.

Figures 8A, 8B:
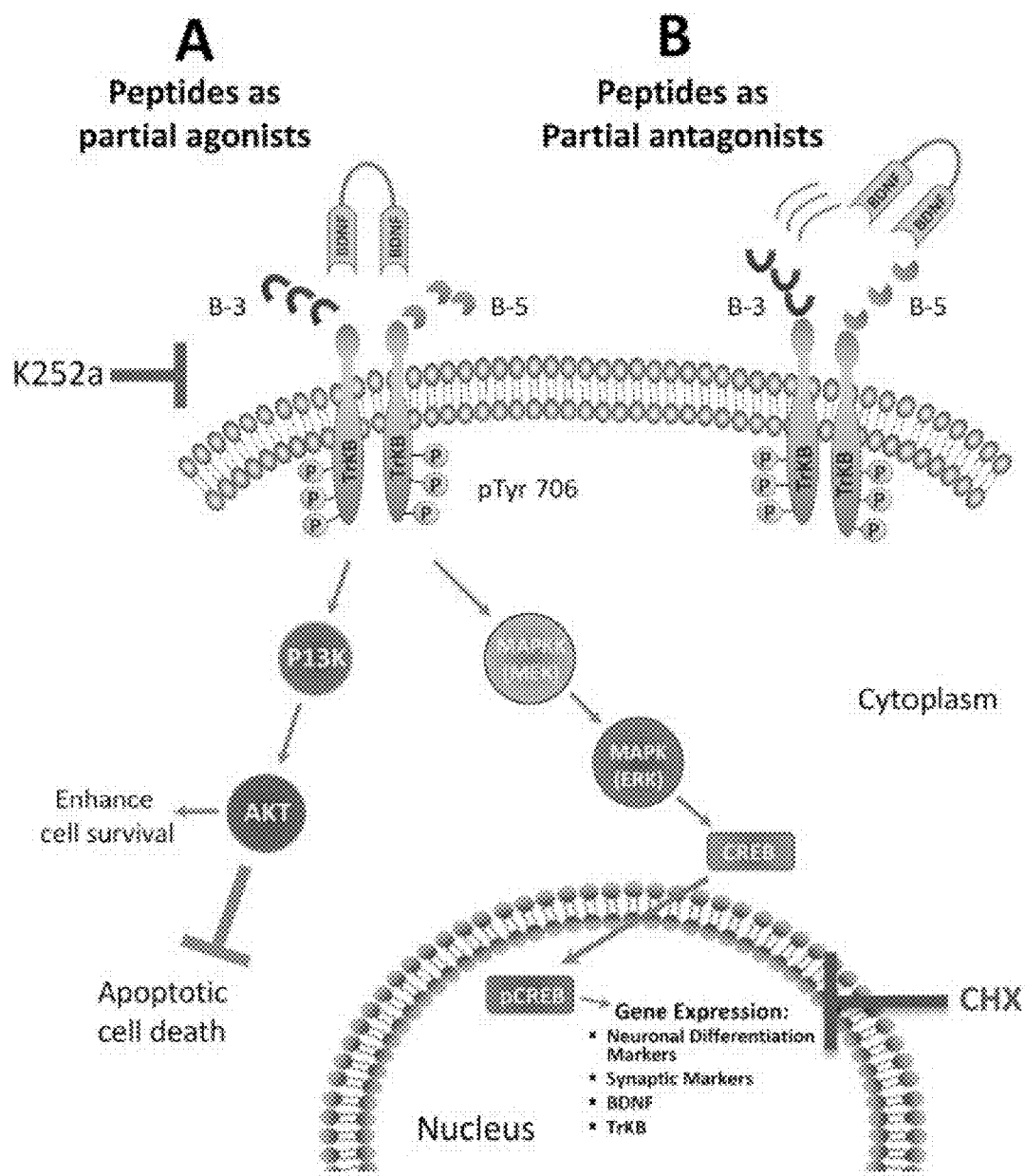

FIGS. 8A and 8B are schematics of the proposed mechanism of action of the BDNF peptides of the present invention were BDNF peptides B-5 and B-3 may interact with or compete for the binding site of BDNF (green) to its transmembrane receptor TrkB (yellow) and, depending on the concentration or the cellular state or condition (i.e., during stress, like in the presence of $H_2O_2$), the peptides could act as partial agonist or partial antagonists.

Figure 9A:
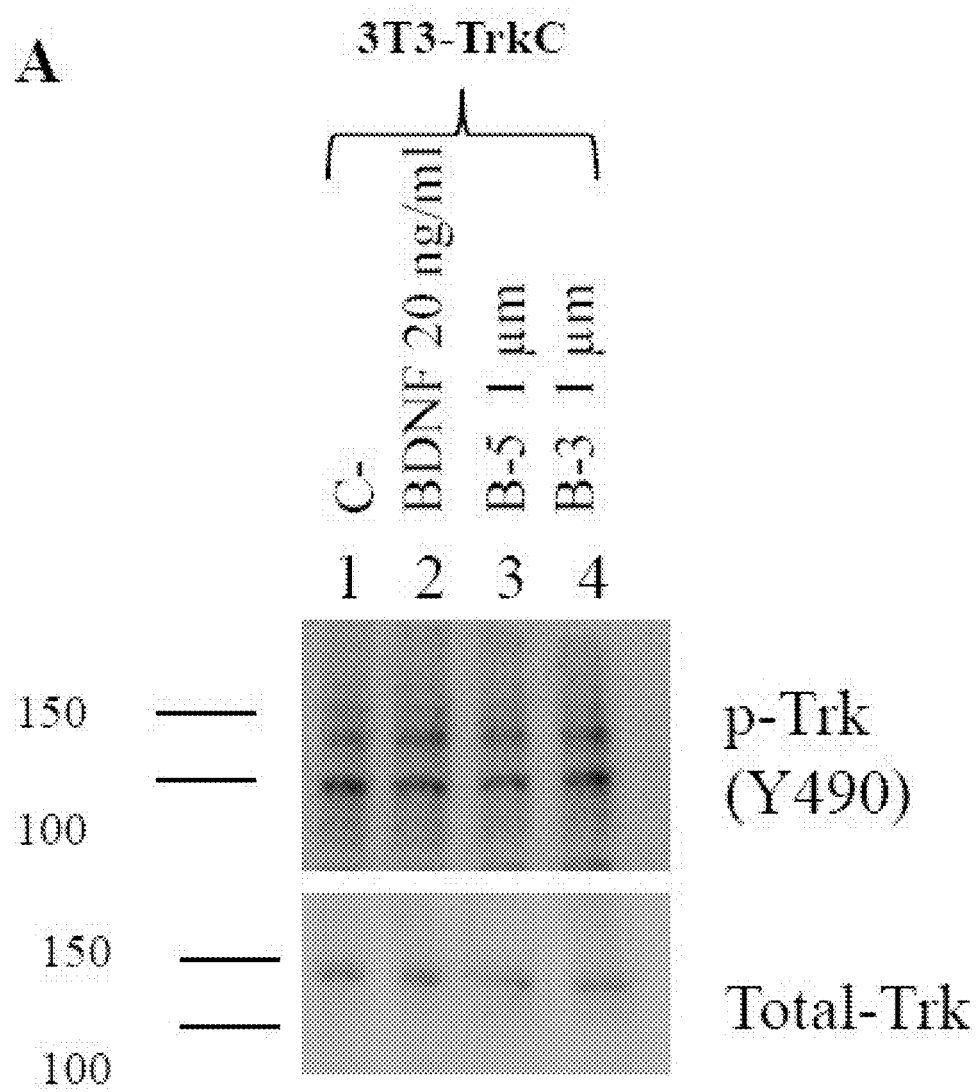

FIG. 9A is a Western blot of anti-pan-phospho-Trk (Y490) and of total TrkC. GAPDH used as a loading control, where neither BDNF (20 ng/mL) nor peptides B-5 (1 µM) and B-3 (1 µM) were able to modify the expression of TrkC in TrkC stably-expressing NIH-3T3 fibroblast cells.

Figure 9B:
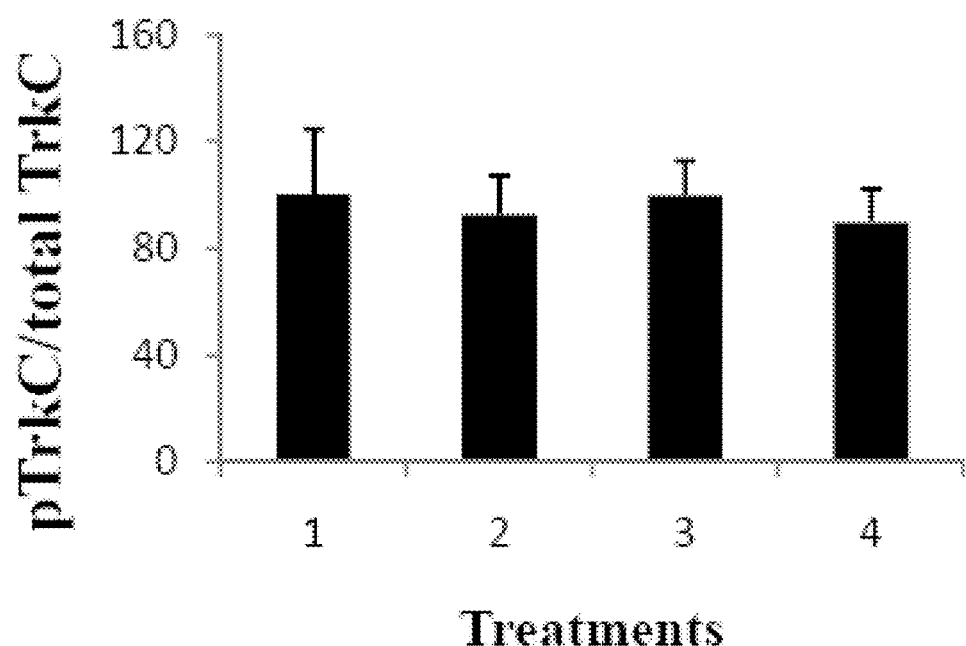

FIG. 9B is a graph of the densitometric quantitation of the Western blots for pTrk normalized to total TrkC (after normalizing TrkC to GAPDH), where data are shown as mean±standard deviation, n=3.

DETAILED DESCRIPTION OF THE INVENTION

The present invention comprises five tetra peptides based on different active regions of BDNF that were identified using epitope mapping of neutralizing antibodies. More particularly, the present invention involves five tetra peptides corresponding to amino acid residues 6-9, 71-74, 72-75, 94-97 and 115-118 of human BDNF. These five tetrameric peptides (B-1 to B-5), Peptide B-5 (Ac-I-K-R-G-CONH2), Peptide B-4 (Ac-D-K-R-H-CONH2), Peptide B-3 (Ac-S-K-K-R-CONH2), Peptide B-2 (Ac-I-D-K-RCONH2), and Peptide B-1 (Ac-R-R-G-E-CONH2), were synthesized at Stanford University Protein and Nucleic Acid Research Lab on a commercial basis. All of compounds had 95% of purity and their identity was confirmed by mass spectrometry. The synthetic peptides were soluble in water.

To screen these peptides, primary neuronal cell cultures were used from embryonic day 18 (E18) C57BL/6 mouse hippocampus. At the fourth day in vitro (DIV), the culture medium was exchanged with the medium containing the peptides. The primary neuronal cultures were established as taught in the art (see, e.g., Cardenas-Aguayo Mdel, Santa-Olalla et al. 2003, hereby incorporate by reference). Briefly, C57BL/6 time pregnant E18 female mice from Charles River Labs were anesthetized and killed by cervical dislocation following our Institutional Animal Care and Use Committee (IACUC) regulations and approved protocol. Embryos were removed and placed in cold Hibernate A (available from Brain bits, Springfield, Ill., USA), and all of the following steps were performed in ice-cold Hibernate A, under a stereoscopic (dissection) microscope placed in a laminar flow hood. Fetal brains were removed carefully and fore brain were separated. Then, the hippocampus, including the cortex surrounding the area of the hippocampus, was dissected and cut into small pieces using microsurgical scissors. The cut tissue was transferred with number 5 forceps to 15 ml tubes containing 0.1% trypsin in Versene (Invitrogen Life Technologies, Grand Island, N.Y., USA) and incubated for 15 min at 37° C. followed by inactivation with 10% fetal bovine serum (FBS) in Neurobasal complete medium (Neurobasal Medium supplemented with 2× B-27, 0.30% glutamine, and penicillin/streptomycin 0.1 mg/ml and 0.1 U/ml respectively). All medium components were purchased from Invitrogen, Grand Island, N.Y., USA. Every 72 hours the medium was replaced and supplemented with fresh medium with or without a test peptide. Cells were maintained in an incubator at 37° C. at 5% CO2/95% atmospheric air.

For recovering proteins, cells were seeded in 6-well dishes coated with poly-D-lysine (SigmaAldrich, St. Louis, Mo., USA), 50 µg/ml for an overnight, at a density of 1×10$^6$ cells/well. For immunocytochemistry, cells were seeded onto 5 mm cover slips coated with poly-D-lysine at a density of $7\times10^4$ cells/well in 100 µl Defined Medium in 96 well plates. The cells were cultured for four days in vitro prior to the beginning of the treatment with the peptides. The treatment with the peptides was done for five days (starting at DIV 4 and finishing at DIV 9). The culture medium was exchanged completely at the beginning of the treatment with a test peptide (at DIV4), and every 72 h until DIV 9.

To study the activation of the TrkB receptor with BDNF and/or with the peptides, NIH 3T3 cells were used, stably transfected with the TrkB receptor (obtained from Montréal Neurological Institute, Montréal, Québec, Canada). The cell culture medium used for this cell line was: DMEM-high glucose, 10 percent normal calf serum, 1 percent glutamax, 1 percent sodium pyruvate, 1 percent penicillin-streptomycin; supplemented with the selection antibiotic G418 in a final concentration of 100 µg/ml (to guaranty the stable expression of the Trkb transgene). All Medium components were purchase from Gibco Life Technologies, Invitrogen, Grand Island, N.Y., USA.

Peptides were dissolved in water in serial dilutions of 10 mM, 1 mM, 100 µM and 10 µM from which the necessary amount was added directly to the culture medium to a final concentration of 0.05 µM, 1 µM, or 10 µM. The BDNF (Peprotech, N.J., USA) was used as a reference in concentrations of 20 ng/ml (0.79 nM) and 100 ng/ml (3.95 nM). Cycloheximide (CHX) (Sigma-Aldrich, St Louis, Mo., USA) was used for blocking protein synthesis. CHX original stock was 100 mg/ml (355.4 mM) in DMSO; from a second stock of 35.54 mM in DMSO, the dilutions were made to the final concentrations of 100 µM. The K252a (CALBIOCHEM/EMD) was used to inhibit the TrkB Receptor. From a stock of 100 µM in DMSO, K252a was diluted to a final working concentration of 200 nM. The E18 primary hippocampal cells were pre-treated with CHX or K252a 1 h prior to the addition of the peptides or BDNF and a time course of these treatments for 15 min, 60 min and 2 days was studied.

After 5 days of treatment, cells seeded on cover slips were fixed in 4% paraformaldehyde (Electron Microscopy Sciences, Pa., USA) for 30 min at room temperature, and then washed 2× in PBS for storage at 4° C. prior to staining. Cells were permeabilized in 0.2% Triton-X-100 in PBS for 30 min at 25° C. and incubated in blocking buffer (1% BSA w/v, 0.2% Triton-X-100 v/v in PBS) for 60 min at 25° C. The cells were then incubated with primary antibodies at the appropriate dilutions in blocking buffer at 4° C. for 16 h, washed 3×10 min with 0.2% Triton X100 in PBS, and incubated with fluorescently-labeled secondary antibodies diluted in blocking buffer for 1 h at 25° C. in the dark. Cover slips were washed 3×10 min in 0.2% Triton X-100 in PBS and mounted on glass slides with GelMount (Biomeda, Foster City, Calif., USA). The following primary antibodies were used: rabbit polyclonal anti-GFAP (1:500; Sigma-Aldrich, St. Louis, Mo., USA); rabbit polyclonal anti-NFM (1:200; Chemicon/Millipore, Billerica, Mass., USA); mouse monoclonal anti-NeuN (1:300; Millipore, Billerica, Mass., USA); rabbit polyclonal anti-Tuj-1, 0-III-tubulin (1:800; Covance, Emeryville, Calif., USA); mouse monoclonal SMI 52 to the adult isoforms of MAP-2, MAP2a,b (1:1000; Covance, Emeryville, Calif., USA); rabbit polyclonal anti-synapsin I (1:2000; Stressgen, Farmingdale, N.Y., USA); and rabbit monoclonal anti-PSD95 (1:100; Cell Signaling, Danvers, Mass., USA). Secondary goat anti-mouse and anti-rabbit IgGs conjugated with AlexaFluor 594 were used at 1:1000 (Molecular Probes, Carlsbad, Calif., USA). The nuclei were stained with 1 µM TOPRO in PBS (Invitrogen, Grand Island, N.Y., USA). Mounted cover slips were examined using 40× oil immersion objective of a Nikon 90i fluorescent microscope equipped with Nikon C1 three-laser confocal system and a Nikon DS U1 digital camera, and analyzed with EZ-C 1 Viewer Image software, Version 6.0.

Following treatment in 6-well plates, cells were washed 2× in glucose buffered saline, GBS (5.4 mM KCl, 138 mM NaCl, 22 mM glucose, and 2 mM Na—KPO pH 7.2), and then lysed by 5 min incubation on ice in 100 or 150 µl of ice-cold RIPA buffer (PBS, 1% w/v NP-40 from Fisher Scientific, 0.1% w/v SDS, and 0.5% w/v sodium desoxycholate) containing 1 mM AEBSF (Gold Biotechnology, St. Louis, Mo., USA), 10 µg/ml aprotinin (Sigma-Aldrich, St. Louis, Mo., USA), and 20 µg/ml of leupeptin and pepstatin (US Biochemicals, Cleveland, Ohio, USA), and phosphatase inhibitors: NaF, Na orthovanadate, (3-glycerophosphate, and microcystein (Sigma-Aldrich, St. Louis, Mo., USA). Extracts were prepared by collecting and pooling a minimum of 2 wells by scraping, and lysates were centrifuged at 20,000×g for 10 min at 4° C. Protein concentration of each cell lysate was determined using the BCA kit (Thermo Scientific, Rockford, Ill., USA). The lysates (7.5-20 µg total protein) were separated on 10% SDS-PAGE gels (except for BDNF where 12% gels were employed) and transferred to 0.45 µm PVDF membrane (Pall, Pensacola, Fla., USA) for probing with antibodies as noted. Blots were blocked for 1 hr at 37° C. in 1× TBST (0.05% Tween 20 in TBS) containing 5% w/v blotting grade dry milk (Bio-rad, Hercules, Calif., USA), incubated in primary antibody overnight in blocking buffer at 4° C., washed 3×10 min in TBST at room temperature, followed by incubation with secondary antibody, i.e., peroxidase-conjugated anti-mouse or anti rabbit IgG (Jackson ImmunoResearch Laboratories, West Grove, Pa., USA) diluted in blocking buffer. Blots were washed 3×10 min in TBST and immunoreactive protein bands were visualized with enhanced chemiluminescence (ECL) reagents (Pierce, Rockford, Ill., USA). The ECL films of the blots were scanned and analyzed using Multi Gauge software version 3.0 (Fujifilm, Tokyo, Japan).

The following primary antibodies were used: rabbit polyclonal anti-NFM (1:1000; Chemicon/Millipore, Billerica, Mass., USA); mouse monoclonal anti-NeuN, clone A60 (1:500; Millipore, Billerica, Mass., USA); rabbit polyclonal anti-Tuj-1, (3-III-tubulin (Covance; 1:800, Emeryville, Calif., USA); mouse monoclonal SMI 52 to the adult isoforms of MAP-2, MAP2a,b (1:1000; Covance, Emeryvilly, Calif., USA); rabbit polyclonal anti-Synapsin I (1:2000; Stressgen, Farmingdale, N.Y., USA); rabbit monoclonal anti-PSD95 (1:1000; Cell signaling, Danvers, Mass., USA); anti tau 92e (1:10000); mouse monoclonal anti-BDNF (1:1000; Calbiochem, Gibbstown, N.J., USA); rabbit polyclonal anti-TrkB (total) (1:500; Santa Cruz Biotechnology, Santa Cruz, Calif., USA); rabbit polyclonal anti-pTrkB (Tyr706) (1:400; Santa Cruz Biotechnology, Santa Cruz, Calif., USA), TrkC (1:1000; Cruz Biotechnology, Santa Cruz, Calif., USA); and pTrkY490 (1:500; Upstate USA Inc., Charlottesville, Va., USA). For loading control, the blots were developed with rabbit polyclonal antibody to GAPDH (1:2000; Santa Cruz Biotechnology, Santa Cruz, Calif., USA).

Evaluation of cell death and cell viability was performed using the LDH kit (Promega, Madison Wis., USA), following manufactures instructions. Percentages of cell death and cell viability were plotted separately.

Statistical analyses were conducted using SPSS version 16.0 (© SPSS Inc., 1989-2007, Chicago, Ill., USA), Sigma Plot version 7.0 (San Jose, Calif., USA), and GraphPad Prism version 5.0 (GraphPad Software Inc., La Jolla, Calif., USA). Data are presented as mean plus standard deviation. For analysis involving multiple groups, one-way ANOVA with post hoc Fisher's, Tukey's, or Bonferroni's test was used. For all other comparisons (including inter-group comparisons), Student's t-test was used. For all purposes, $p<0.05$.

EXAMPLE

Figure 1B:
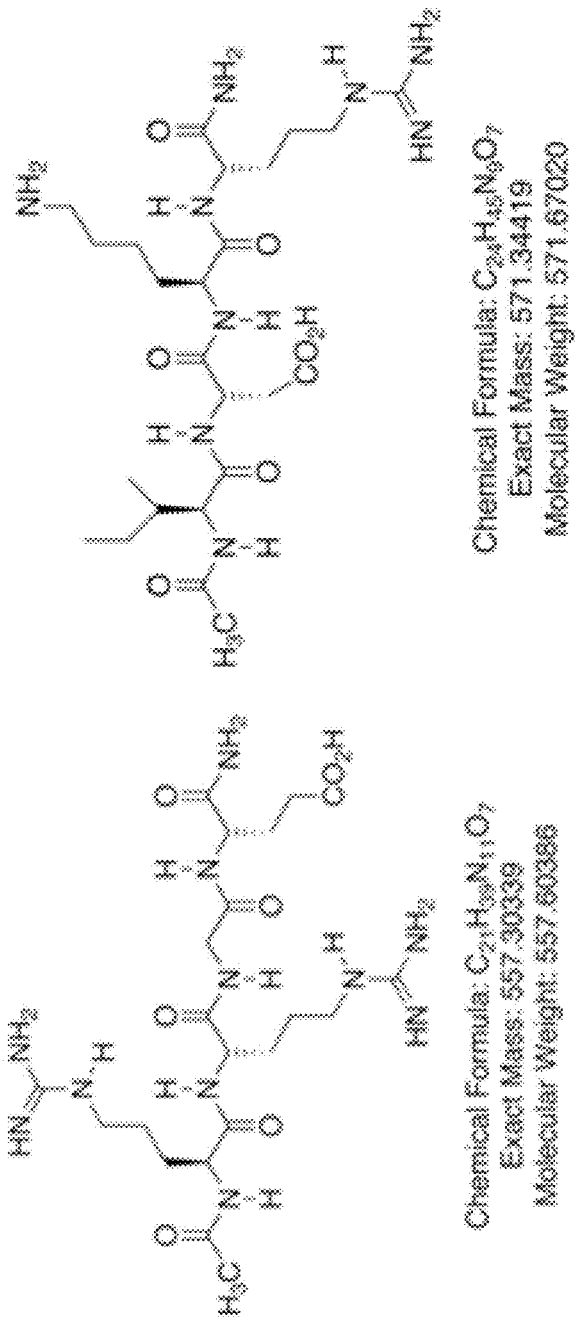
FIG. 1B is a schematic of the chemical structures of the BDNF peptides of the present invention.
Figure 1B:
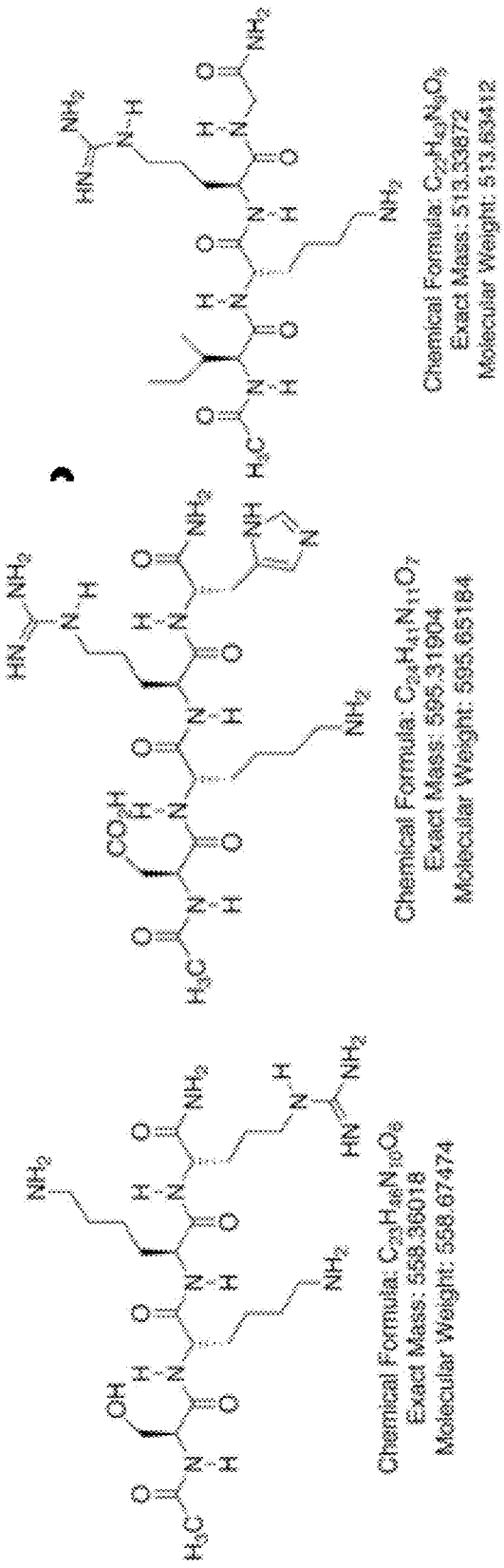

Referring to FIGS. 1A and 1B, a total of 5 tetrapeptides were synthesized at a 95-99% of purity after HPLC based on epitope mapping of neutralizing antibodies to human BDNF. Peptides B-1 to B-5 were N-terminally acetylated and C-terminally amidated, as seen in FIG. 1B. The sequences of these peptides are as follows: Peptide B-5 (SEQ ID NO: 1: Ac¬K-R-G-CONH2 corresponding to amino acids (AAs) 243-246 of pro BDNF and AAs 115-118 of BDNF), molecular weight 513.63; Peptide B-4 (SEQ ID NO: 2: Ac-D-K-R-H-CONH2 corresponding to AAs 200-203 of pro BDNF and AAs 72-75 of BDNF), molecular weight 595.65; Peptide B-3 (SEQ ID NO: 3: Ac-SK-K-R-CONH2 corresponding to AAs 222-225 of pro BDNF and AAs 94-97 of BDNF), molecular weight 558.67; Peptide B-2 (SEQ ID NO: 4: Ac-I-D-K-R-CONH2 corresponding to AAs 193-196 of pro BDNF and AAs 71-74 of BDNF), molecular weight 571.67; and Peptide B-1 (SEQ ID NO: 5: Ac-R-R-G-E-CONH2 corresponding to AAs 134-137 of pro BDNF and AAs 6-9 of BDNF), molecular weight 557.6 (as seen in FIG. 1A). All peptides were found to be water soluble.

To study any toxic effect of the peptides, mouse E18 primary hippocampal neurons were treated with the five BDNF peptides individually for up to 5 days at different doses [5 nM, 25 nM, 50 nM (data not shown), 100 nM (0.1 µM), 1000 nM (1 µM), and 10,000 nM (10 µM)]. Phase contrast photomicrographs revealed no gross morphological changes in cells treated with the BDNF peptides, as compared to the vehicle-treated or BDNF-treated cells (see FIG. 2A). Accordingly, there was no significant change in the viability of cells treated with any of the peptides as evaluated by the lactate dehydrogenase (LDH) assay (see FIG. 2B). However there was a significant reduction in cell death when cells were treated with Peptide B-3 (0.1 µM, ANOVA, p=0.012, post-hoc tests, p=0.000, Student's t test, p=0.0061; 1 µM, ANOVA, p=0.012, post-hoc test, p=0.033, Student's t test, p=0.0398) and Peptide B-1 (1 µM ANOVA, p=0.012, post-hoc test, p=0.001, Student's t test, p=0.0239) in comparison to vehicle treated cells (control, C). Thus, the five BDNF peptides were not toxic for the E18 hippocampal cells. Only three peptides (B-5, B-4 and B-3) were selected for further characterization.

Immunocytochemical studies revealed that peptide B-5 at a concentration of 1 µM induced an increase in the expression of MAP2 (a dendritic marker), 0-III-tubulin (an early neuronal marker), NFM (an early neuronal and axonal marker), and NeuN (a late neuronal marker) in mouse E18 hippocampal neurons after 5 days of treatment (FIG. 3A), as compared to vehicle treated cells (FIG. 3C). The increase in MAP2, NFM and NeuN staining with peptide B-5 was similar to the one obtained when cells were treated with BDNF, 20 ng/ml, (0.79 nM) (FIG. 3B), suggesting that the peptides could mimic at least in part the effects of the parent growth factor (BDNF). The fact that the cells treated with Peptide B-5 were NeuN-positive could mean that these cells were terminally differentiated and, for that reason, they could also be functional, since they were also positive for other neuronal markers, such as 0-III-tubulin and MAP2. Peptide B-3 had similar effects on the expression of the neuronal markers (data not shown).

To biochemically study the effect of BDNF peptides in inducing expression of neuronal markers, protein samples were recovered from cells treated with peptides B-5, B-4, B-3, or vehicle for five days. As a positive control, protein samples were collected from cells treated with BDNF at 20 ng/ml (0.79 nM) or 100 ng/ml (3.95 nM) (FIG. 3D, E). Western blots of the cell lysates were developed with antibodies to Synapsin I (presynaptic marker), PSD95 (postsynaptic marker), NeuN (late neuronal marker), NFM (early neuronal marker), MAP2 (dendritic marker), 0-IIItubulin (early neuronal marker), and tau 92e (axonal marker). The densitometric analysis showed that peptides B-5 and B-4 induced a significant increment in the expression of the postsynaptic marker PSD95 (p=0.003, ANOVA for B-5 1 µM and p=0.024, ANOVA for B-4 0.1 µM), similar to the increase obtained by the treatment with BDNF (at 20 and 100 ng/ml, p=0.039, ANOVA and p=0.012, ANOVA, respectively) (FIG. 3E). Peptides B-5 (1 µM; p=0.002, ANOVA), B-4 (0.1 µM; p=0.043, ANOVA) and B-3 (0.1 µM; p=0.038, ANOVA and 1 µM; p=0.05, ANOVA) increased the expression of NeuN. Peptide B-5 (0.1 µM; p=0.032, ANOVA) increased NFM expression in a similar way to the treatment with BDNF (20 ng/ml and 100 ng/ml; p=0.011 and p=0.034, ANOVA, respectively). MAP2 expression increased significantly with B-5 (0.1 µM; p=0.009, ANOVA) treatment. Only peptide B-5 (1 µM) induced an increase in the levels of 0-IIItubulin as compared to vehicle-treated cells for five days, but this increase was not significant. Neither BNDF nor peptides B-3, B-4 or B-5 had any significant effect on the level of tau (detected with 92e antibody), as seen in FIGS. 3D and 3E.

In order to evaluate the potential neuroprotective effect of BDNF peptides, the primary E18 hippocampal cells were challenged with 0, 60, 80 and 100 µM H2O2 for 6 hours, and then cells were washed with culture medium and fresh culture medium was added containing the peptides B-5 or B-3 or BDNF or BDNF plus B-3 (see FIGS. 4A and 4B). After 24 hours, the cell viability was assayed by the LDH method. Cells treated with $H_2O_2$ showed a significant increase in cell death (ANOVA, p<0.0001) (see FIG. 4A) with a concomitant reduction in cell viability (see FIG. 4B) (ANOVA, p<0.0001). The cells treated with BDNF after being exposed to $H_2O_2$ showed some reduction in cell death when compared to control medium treated cells, however, this was not statistically significant for most except for BDNF with 60 µM $H_2O_2$ treatment (0 µM $H_2O_2$, ANOVA, p=0.9377, Student's t test, p=0.2700; 60 µM $H_2O_2$, ANOVA, p=0.0304, Student's t test, p=0.1076; 80 µM $H_2O_2$, ANOVA, p=0.3699, Student's t test, p=0.3094; 100 µM $H_2O_2$, ANOVA, p=0.3764, Student's t test, p=0.9519). Conversely, BDNF increased cell viability significantly at 0 and 60 µM $H_2O_2$ but was not effective at high $H_2O_2$ concentrations (80 µM and 100 µM) (0 µM $H_2O_2$, ANOVA, p=0.3167, Student's t test, p=0.0124; 60 µM $H_2O_2$, ANOVA, p=0.0675, Student's t test, p=0.1072; 80 µM $H_2O_2$, ANOVA, p=0.5762, Student's t test, p=0.7943; 100 µM $H_2O_2$, ANOVA, p=0.4162, Student's t test, p=0.9508). These effects were enhanced by the combination of BDNF with Peptide B-3 in cells treated with 0, 60, and 80 µM but not 100 µM $H_2O_2$ (Cell death, 0 µM $H_2O_2$, ANOVA, p=0.7534, Student's t test, p=0.7876; 60 µM $H_2O_2$, ANOVA, p=0.0247, Student's t test, p=0.0256; 80 µM $H_2O_2$, ANOVA, p=0.4880, Student's t test, p=0.0189; 100 µM $H_2O_2$, ANOVA, p=0.1603, Student's t test, p=0.5894; Cell viability, 0 µM $H_2O_2$, ANOVA, p=0.6739, Student's t test, p=0.0074; 60 µM $H_2O_2$, ANOVA, p=0.0129, Student's t test, p=0.0790; 80 µM $H_2O_2$, ANOVA, p=0.1956, Student's t test, p=0.0573; 100 µM $H_2O_2$, ANOVA, p=0.2682, Student's t test, p=0.4745). These results suggest that peptide B-3 potentiates the neuroprotective effect of BDNF but alone is not sufficient to exert a significant effect. Peptide B-5 alone had a moderate effect in reducing the percentage of cell death when the hippocampal cells were treated with 80 µM of $H_2O_2$ (0 µM $H_2O_2$, ANOVA, p=0.1119, Student's t test, p=0.1911; 60 µM $H_2O_2$, ANOVA, p=0.2057, Student's t test, p=0.7086; 80 µM $H_2O_2$, ANOVA, p=0.4007, Student's t test, p=0.0061; 100 µM $H_2O_2$, ANOVA, p=0.4124, Student's t test, p=0.6888); also it significantly increased the cell viability with 60 and 80 µM of $H_2O_2$ (0 µM $H_2O_2$, ANOVA, p=0.6015, Student's t test, p=0.2478; 60 µM $H_2O_2$, ANOVA, p=0.3191, Student's t test, p=0.0084; 80 µM $H_2O_2$, ANOVA, p=0.7923, Student's t test, p=0.0229; 100 µM $H_2O_2$, ANOVA, p=0.7709, Student's t test, p=0.0717).

To investigate the molecular mechanism by which the BDNF peptides promoted neurogenic/neurotrophic activities, the hippocampal primary cultured neurons were treated with the peptides or BDNF for five days and compared with the control medium treated cells. Peptides B-5, B-4 and B-3 induced the expression of BDNF, probably potentiating its pathway (see FIGS. 5A and 5B). The strongest induction of the expression of BDNF was produced by Peptide B-5 at a concentration of 0.1 µM (ANOVA, p<0.0003); at 1 µM this effect of Peptide B-5 was lost. However, peptide B-3 at 1 µM but not at 0.1 µM induced an increase in the expression of BDNF (ANOVA, p<0.027).

The effect of 1 h treatment by these two peptides on the level and activation of TrkB receptor in the hippocampal primary cultured neurons to further understanding the feedback mechanism of action of the BDNF peptides. Peptides B-5 and B-3 induced a weak activation of TrkB phosphorylation in comparison to the activation of this receptor by BDNF in primary E18 hippocampal cells (see FIGS. 5C and 5D). A protein band at 145 kDa corresponding to the phosphorylation of TrkB receptor at tyrosine 706 which is one of the sites that gets rapidly phosphorylated on exposition of the ligand of this receptor for one hour was observed. The level of total TrkB receptor and the level of GAPDH as a loading control were used as references. The normalization of the phosphorylated TrkB with total TrkB showed a strong and significant activation of TrkB by BDNF (ANOVA, p<0.0001) as expected, and a relatively weak activation of the receptor by B-5 and B-3 (ANOVA, p=0.0085 and p=0.0237 respectively). The fact that BDNF peptides are able to activate weakly the TrkB receptor suggests that they could act as partial agonists. The TrkB levels were increased on treatment with B-5 and B-3, almost reaching the significance level with B-5 (ANOVA, p=0.057) (see FIGS. 5C and 5D).

The NIH 3T3 fibroblasts stably expressing the TrkB receptor were vehicle-treated or treated with BDNF peptides B-5 and B-3 at a concentration of 1 µM or with BDNF at a concentration of 20 ng/ml (0.79 nM) for 5, 15 or 60 min (FIG. 5E, F). During 60 min of treatment with peptides B-5 and B-3, a marked increase (ANOVA, p<0.05) in the expression of the receptor TrkB with both peptides was observed (FIGS. 5C and 5D). The effect was time-dependent and was pronounced at 60 min treatment. These data support the previous findings shown above in FIGS. 5C and 5D, where an increase in TrkB receptor in E18 primary hippocampal cells after treatment with Peptide B-5 and B-3 was found. The effect on the increase in expression of TrkB by Peptides B-5 and B-3 could be the way in which the peptides potentiate the BDNF pathway to avoid saturation of the receptors, and/or promote their neurotrophic effect by increasing the expressions of both BDNF (FIGS. 5A and 5B) and TrkB (FIGS. 5C through 5F).

To further confirm the activation of the TrkB receptor by the peptides, the mouse primary E18 hippocampal cells were penetrated with the Trk family inhibitor K252a for 1 h and then added the growth factor BDNF (20 ng/ml) or the peptides B-5 or B-3 (at 1 µM) for 5 min and compared to vehicle-treated cells used as a control (C). By Western blots, a clear inhibition of the phosphorylation of TrkB at Tyrosine 706 by K252a (see FIGS. 6A and 6B) was found. The increase in the phosphorylation of the TrkB receptor was significant for the treatment with B-5 and B-3 and BDNF (B-5, 1 µM, ANOVA, p=0.0341; B-3, 1 µM, ANOVA, p=0.001; BDNF, 20 ng/ml, ANOVA, p=0.0003), but when cells were pretreated with K252a, there was a dramatic reduction in the activation of this receptor. These results confirmed that the peptides activated the TrkB receptor, and that this activation can be blocked by the Trk inhibitor, K252a. Total TrkB is shown as a reference, but a significant change in its expression was not seen. Since the treatment with the peptides was for a very short time (5 min), changes in the level of TrkB expression were not expected. There was an apparent specificity of the peptides B-5 and B-3 for activating TrkB receptor since its activity was tested on NIH 3T3 cells stably expressing TrkC, and neither the peptides nor BDNF were able to activate this receptor, which is normally activated by its ligand NT-3, as seen in FIGS. 9A and 9B.

To evaluate a possible competitive role of the peptides in the activation of TrkB receptor by BDNF, a fibroblast (NIH 3T3) cell line stably expressing the TrkB receptor was used. Cells were vehicle-treated or treated with BDNF 1 ng/ml (0.04 nM) in the presence or absence of 0.05 µM to 10 µM B-5 or B-3 for 15 min (FIG. 7A). Both B-5 and B-3 showed a significant competitive inhibition (post-hoc tests, p<0.001) of the activation of TrkB receptor by BDNF, and the effect was dose-dependent, suggesting a role of the peptides as partial antagonists of the BDNF pathway since they competed for the activation of the TrkB receptor but they did not block completely its activation by BDNF (FIGS. 7A and 7B). As observed in primary neuronal cultures (shown in FIGS. 5C and D), the treatment with the peptides alone for 15 min induced a weak but significant activation of TrkB receptor when compared to control (ANOVA, p<0.001).

To evaluate whether the effect of B-5 and B-3 in induction of the expression of BDNF and TrkB was via the activation of the TrkB receptor and required signal transduction via TrkB and new protein synthesis, mouse embryonic E18 cultured hippocampal cells were pre-treated with the protein synthesis inhibitor, cycloheximide (CHX) or the Trk inhibitor K252a for 1 h, and then added Peptide B-5 at a concentration of 0.1 µM (the dose that gave the maximum induction of BDNF expression, FIGS. 5A and B) or BDNF 20 ng/ml as a positive control (FIG. 7C,D). A time course of these treatments was studied with Peptide B-5 or BDNF for 15 min, 60 min and two days. At two days there was a significant (ANOVA, p<0.05) inhibition of the increase in the expression of BDNF and of TrkB by the Peptide B-5 in the presence of CHX; and there was no more significant induction of the expression of either BDNF or TrkB by B-5 in cells treated with the Trk inhibitor (K252a) (FIGS. 7C and 7D). Since the effect of BDNF peptides was not completely blocked by K252a, there is a possibility that these peptides activate alternate pathways that lead to expression of BDNF and TrkB.

On the basis of these results, BDNF peptides likely compete with BDNF for the activation of the receptor TrkB (phosphorylation at Tyr 706), and modulate its activity in a partial agonist/antagonist way (see FIGS. 8A and 8B). FIG. 8A is a schematic showing the partial agonistic role of the peptides and that the peptides favor the activation of the TrkB receptor, and in the presence of BDNF, they synergize with it. Once the TrkB receptor gets activated, it is dimerized and autophosphorylated (one of the residues that gets phosphorylated is the Tyr 706) and the signal is transduced. The cascades that could be activated by the peptides include the differentiation pathway through MAPK and pCREB regulating gene expression of markers of neuronal phenotype and plasticity, and also the expression of BDNF and TrkB, giving the possibility of a feedback mechanism. The other cascade that could be activated by the peptides is the survival one, in which PI3K and AKT participate to enhance survival and inhibit cell death. FIG. 8B shows the partial antagonistic role of the peptides where the peptides compete with BDNF for the activation of the receptor blocking the TrkB activation by BDNF and its signal transduction pathway. The sites where the TrkB inhibitor K252a and the protein synthesis inhibitor CHX can block the pathway are shown with a grey and red bar, respectively.

Alternatively, they might also activate other receptors, which may be further investigated. Once the TrkB receptor is active, the signal transduction cascade could activate either PI3K or AKT pathway linked to survival, like in the case of the cells exposed to H2O2, or the MAPK and pCREB pathway that leads to induction of transcription of first early response genes and later, neuronal and synaptic markers. The increase in expression of BDNF and TrkB by Peptides B-5 and B-3 probably work like a feedback system. The inhibitor K252a blocks the activation of TrkB at the beginning of the pathway (see FIG. 8), and CHX blocks the protein synthesis at the end of the pathway.

Therapeutic modulation of BDNF levels thus remains a promising treatment strategy for neurological and psychiatric disorders in which the levels of BDNF are dysregulated. For the above mentioned reasons, the development of small molecules that mimic the effect of BDNF, and depict enhanced permeability and stability can be very useful in the process of generating new drugs. The development of peptide mimetics of BDNF allows simple and controlled modulation of neurotrophic factor activities. The present study demonstrates that the BDNF tetrapeptides, in particular B-5 and B-3, corresponding to active regions of BDNF, are neurogenic and neurotrophic, and can modulate BDNF activity in a partial agonistic/antagonistic way, and by increasing the expression of BDNF and TrkB. The increase in the expression of BDNF suggests a feedback mechanism, and it could be due to an increase in BDNF secretion, which implies that the peptides could be acting as secretagogues (molecules that induce the secretion of other molecules).

Given that the compounds of the present invention are short peptide mimetic molecules of the neurotrophic factor, in most of the cases they should be able to cross the BBB when administered peripherally. In contrast to the non-peptide origin of the small molecules previously used for activating TrkB pathway, these compounds (B-1 to B-5) which also modulate this pathway, are tetrapeptides. These peptides compare favorably to the BDNF derived cyclic peptides generated by others.

All of the peptides according to the present invention were found to be non-toxic to primary cultured hippocampal cells, and were able to induce the expression of neuronal markers. These findings suggest the potential therapeutic use of these peptides in neurodegenerative diseases such as AD and other cognitive disorders. In addition, B-3 showed neuroprotective effect against $H_2O_2$ induced toxicity in combination with BDNF. The fact that peptide B-3 and BDNF together show an additive effect on the survival of the cells exposed to $H_2O_2$ in comparison to the response elicited by BDNF or B-3 alone implies that B-3 could be acting through an alternative pathway besides the BDNF signaling pathway. This is in accordance with the proposed mechanisms of previously reported small molecules that mimetize partially the functions of BDNF.

The present invention demonstrates that the novel BDNF peptides have both functions: partial agonists or partial antagonists. They act as agonist when they synergize with BDNF to protect the cells against oxidative stress, and they act as antagonists when they compete with BDNF to activate the TrkB receptor. A partial agonist is an agent that elicits a maximum response that is less than that of an agonist and acts as an antagonist in the presence of full agonist, while in the absence of a full agonist, partial agonists show functional agonist activity, binding to the receptor to produce a response. Thus, it is possible that the peptides act differently depending on their concentration comparing to the levels of the original ligand (BDNF) or depending on the conditions, e.g., whether the cell is under stress or not. Evidence suggests that excess BDNF is involved in the pathogenesis of epilepsy, mania and autism. Pharmacologic agents that can decrease BDNF-TrkB pathway signaling partially or to a certain extent, may be therapeutic for these diseases since blocking BDNF-TrkB pathways with complete TrkB antagonists can lead to undesirable effects. A fine regulation of this pathway is thus warranted that can be achieved with the use of small molecules (like the BDNF peptides in this study) that can work both as partial agonist and antagonist leading to an optimal balance of this cascade.

In general, the present invention was directed toward a small molecule that could mimic the neuroprotective effects of the complete molecule of the growth factor without causing adverse effects associated with the original ligand. It is likely that these compounds do not activate the pain related pathway associated to BDNF treatment, because these are small molecules that mimetize BDNF and they show activation of TrkB receptor as its principal pathway; the peptides did not activate NT3/NT4 receptor, TrkC. These peptides generated a moderate activation of the TrkB receptor as compared with the activation achieved with the complete growth factor, BDNF, at the time points evaluated, but it is possible that the peptides had a temporal kinetics different than that of BDNF, and it may take longer times to reach the maximum activation of the TrkB receptor, but this remains for further evaluation.

The present application appears to be the first report of the role of BDNF in protection against oxidative stress caused by $H_2O_2$ in primary hippocampal neurons. Nonetheless, there are a few reports which mention that BDNF could enhance survival of $H_2O_2$ stressed cells. The prevention of oxidative stress and the reduction in ROS are considered to be promising approaches for neuroprotection in neurodegenerative diseases. In the present invention, the combination of BDNF plus one of the BDNF peptides (i.e., B-3) was more potent in enhancing the survival of hippocampal cells previously exposed to $H_2O_2$, probably acting in a partial agonistic way. Small molecules that mimic a particular ligand, like in the case of the peptides of the present invention, can bind to their receptors and disrupt protein-protein interactions inhibiting the functions they mediate, or they could act as activating ligands, though there may be differences from the natural ligand with respect to the coupling and kinetics of the induced signaling. The differential activation of downstream signaling by the interaction with ligands and receptors may have an active involvement in the partial agonistic/antagonistic roles of the BDNF peptides used in this study.

The proposed mechanism of action of the BDNF peptides, B-5 and B-3, is that they may interact or compete for the binding site of BDNF to its transmembrane receptor TrkB. Depending on the concentration or the cellular state (for instance, during stress, like in the presence of H2O2), they could act as partial agonist or partial antagonists. Once the TrkB receptor gets activated, it is dimerized and autophosphorylated (one of the residues that gets phosphorylated is the Tyr 706), afterwards, the signal is transduced, and two principal cascades can be activated, the differentiation pathway through MAPK and pCREB, regulating gene expression of markers of neuronal phenotype and plasticity, and regulating also the expression of BDNF and TrkB resulting in the possibility of a feedback mechanism; and the cascade involving PI3K and AKT that regulates survival and cell death. Alternatively BDNF pathway can activate the PLC-y signaling that is involved in activity dependent plasticity.

Brain derived neurotrophic factor has multiple effects in regulating neuronal function and survival, so it is an attractive molecule to target for developing new therapeutic approaches to neurological diseases. Nevertheless, as discussed above, it is still a challenge to deliver this growth factor to the appropriate region of the CNS and to maintain its prolonged expression. For this reason, the peptides of the present invention represent new tools for modulating the BDNF pathway and they could have therapeutic potential in the in vivo models of neurodegenerative diseases that remain to be evaluated. In the case of Alzheimer's disease, previous studies reported the use of small molecule BDNF mimetics that inhibit A3-induced neuritic dystrophy and neuronal death in hippocampal slice cultures, demonstrating the relevant potential role of molecular mimetics in the therapeutics of Alzheimer's disease. Also, previously, ciliary neurotrophic factor (CNTF) derived peptide mimetics have shown beneficial effects in the animal models of neurological diseases. These CNTF derived peptides, which are similar to the BDNF peptides of the present invention, were found to have a beneficial effect on neurogenesis, synaptogenesis, synaptic plasticity, and cognition in mouse and rat models of Alzheimer's disease (Blanchard, Bolognin et al. 2011; Bolognin, Blanchard et al. 2012). Thus, in vivo animal model studies are highly warranted with the BDNF peptides of the present invention.

Applications of small molecule mimetic drugs that target protein kinases involve not only neurological diseases, but also a variety of other disorders including obesity, metabolic syndrome, muscular degenerations, ulcerative lesions, diabetes, and cancer. In the case of cancer, it can be useful to find a molecule that works as an antagonist of Trk receptors, since these receptors by virtue of being involved in the regulation of growth, differentiation and programmed cell death are reported to be involved in oncogenesis. Thus, the BDNF peptides of the present invention, which are only four amino acid long, are nontoxic, and exert neurogenic and neurotrophic effects in neuronal hippocampal cell culture, and, thus, could serve as neurotrophic drugs or act as lead compounds for the development of neurotrophic drugs with enhanced permeability and stability.

What is claimed is:

1. A method of therapeutically modulating the level of brain derived neurotrophic factor in a subject comprising the step of administering a peptide selected from the group consisting of SEQ ID NO: 1, SEQ ID NO: 2, SEQ ID NO: 3, SEQ ID NO: 4, and SEQ ID NO: 5.

2. The method of claim 1, wherein the N-terminal of said peptide has been acetylated.

3. The method of claim 1, wherein the C-terminal of said peptide has been amidated.

4. The method of claim 1, wherein said peptide is characterized by an affinity for the tropomyosin-related kinase-B receptor.

5. The method of claim 1, wherein said peptide induces the expression of brain-derived neurotrophic factor.

6. The method of claim 1, wherein said peptide acts as a partial agonist for brain-derived neurotrophic factor when administered therewith.

7. The method of claim 1, wherein said peptide activates the tropomyosin-related kinase-B receptor in a dose-dependent manner.

* * * * *

SEQUENCE LISTING

```
<160> NUMBER OF SEQ ID NOS: 6

<210> SEQ ID NO 1
<211> LENGTH: 4
<212> TYPE: PRT
<213> ORGANISM: Artificial Sequence
<220> FEATURE:
<223> OTHER INFORMATION: synthesized peptide

<400> SEQUENCE: 1

Ile Lys Arg Gly
1

<210> SEQ ID NO 2
<211> LENGTH: 4
<212> TYPE: PRT
<213> ORGANISM: Artificial Sequence
<220> FEATURE:
<223> OTHER INFORMATION: synthesized peptide

<400> SEQUENCE: 2

Asp Lys Arg His
1

<210> SEQ ID NO 3
<211> LENGTH: 4
<212> TYPE: PRT
<213> ORGANISM: Artificial Sequence
<220> FEATURE:
<223> OTHER INFORMATION: synthesized peptide
```

<400> SEQUENCE: 3

Ser Lys Lys Arg
1

<210> SEQ ID NO 4
<211> LENGTH: 4
<212> TYPE: PRT
<213> ORGANISM: Artificial Sequence
<220> FEATURE:
<223> OTHER INFORMATION: synthesized peptide

<400> SEQUENCE: 4

Ile Asp Lys Arg
1

<210> SEQ ID NO 5
<211> LENGTH: 4
<212> TYPE: PRT
<213> ORGANISM: Artificial Sequence
<220> FEATURE:
<223> OTHER INFORMATION: synthesized peptide

<400> SEQUENCE: 5

Arg Arg Gly Glu
1

<210> SEQ ID NO 6
<211> LENGTH: 247
<212> TYPE: PRT
<213> ORGANISM: Homo sapiens

<400> SEQUENCE: 6

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

-continued

```
Arg Thr Thr Gln Ser Tyr Val Arg Ala Leu Thr Met Asp Ser Lys Lys
    210             215             220

Arg Ile Gly Trp Arg Phe Ile Arg Ile Asp Thr Ser Cys Val Cys Thr
225             230             235             240

Leu Thr Ile Lys Arg Gly Arg
                245
```